United States Patent [19]

Torobin

[11] Patent Number: 4,637,990

[45] Date of Patent: Jan. 20, 1987

[54] HOLLOW POROUS MICROSPHERES AS SUBSTRATES AND CONTAINERS FOR CATALYSTS AND METHOD OF MAKING SAME

[76] Inventor: Leonard B. Torobin, Materials Technology Corporation, 120 Interstate North, Parkway East, Ste. 158, Atlanta, Ga. 30339

[21] Appl. No.: 711,951

[22] Filed: Mar. 14, 1985

Related U.S. Application Data

[60] Continuation-in-part of Ser. No. 639,126, Aug. 9, 1984, and a continuation-in-part of Ser. No. 657,090, Oct. 3, 1984, said Ser. No. 639,126, is a continuation-in-part of Ser. No. 428,923, Sep. 30, 1982, Pat. No. 4,548,196, which is a continuation of Ser. No. 103,113, Dec. 13, 1979, abandoned, which is a division of Ser. No. 59,296, Jul. 20, 1979, abandoned, which is a continuation-in-part of Ser. No. 937,123, Aug. 28, 1978, abandoned, and Ser. No. 944,643, Sep. 21, 1978, abandoned.

[51] Int. Cl.$^4$ .......................... B01J 35/00; B01J 37/00
[52] U.S. Cl. ........................................... 502/10; 502/8; 502/527
[58] Field of Search .......................... 502/8, 9, 10, 527

[56] References Cited

U.S. PATENT DOCUMENTS

| | | | |
|---|---|---|---|
| 2,912,375 | 11/1959 | MacLaren | 208/213 |
| 3,159,568 | 12/1964 | Price et al. | 208/89 |
| 3,202,480 | 8/1965 | Nixon | 23/143 |
| 3,347,798 | 10/1967 | Baer et al. | 252/448 |
| 3,423,489 | 1/1969 | Arens et al. | 264/4 |
| 3,528,809 | 9/1970 | Farnand | 75/222 |
| 3,639,306 | 2/1972 | Sternberg et al. | 260/2.5 B |

List Continued on next page.

FOREIGN PATENT DOCUMENTS

WO86/01147 2/1986 PCT Int'l Appl.

OTHER PUBLICATIONS

Leenaars et al., The Preparation and Characterization of Alumina Membranes with Ultra-fine Pores, Journal of Materials Science, vol. 19, pp. 1077–1088, (1984).

Ward, III et al., Immobilized Liquid Membranes for Sulfur Dioxide Separation, Final Report, Contract No. Ph-36-68-76, Mar. 1970.

Kirk-Othmer, Molecular Seives, vol. 15, pp. 638–668 (19 ).

Reedy: "Selection and Measurement of Microsphere Laser Targets Based on Refraction", J. of Applied Physics, vol. 47, No. 6, Jun. 1976, pp. 2502–2508.

Cutler et al., Lightweight Proppants for Deep Gas Well Stimulation, TerraTek Engineering, TRE 83-18, December 1983, pp. 21–30.

*Primary Examiner*—W. J. Shine
*Attorney, Agent, or Firm*—Perry Carvellas

[57] ABSTRACT

Hollow porous microspheres are used as substrates and containers for catalyst to make microsphere catalysts.

The hollow porous microspheres are made from dispersed particle compositions. The microspheres have a single central cavity, have substantially uniform diameters and substantially uniform wall thickness and the walls of the microspheres have substantially uniform void content, i.e., interconnecting voids, and have substantially uniform distribution of interconnecting voids. The interconnecting voids in the walls of the microspheres are continuous and extend from the outer wall surface of the microsphere to the inner wall surface of the microsphere.

The microsphere catalysts are prepared by coating or impregnating the hollow porous microspheres with a catalyst or by applying a catalyst support to the microspheres and then coating or impregnating the microspheres and catalyst support with a catalyst.

The microsphere catalyst can also be prepared by filling the hollow porous microspheres with a catalyst or catalyst and catalyst support.

The microsphere catalyst can be treated to immobilize the catalyst and can be treated to provide the microsphere with a selective membrane. The microsphere catalyst can be used for a wide variety of catalyst reactions.

54 Claims, 11 Drawing Figures

U.S. PATENT DOCUMENTS

| | | | |
|---|---|---|---|
| 3,674,461 | 7/1972 | Farnand | 75/5 R |
| 3,686,137 | 8/1972 | Gatti | 252/437 |
| 3,792,136 | 2/1974 | Schmitt | 264/44 |
| 3,798,176 | 3/1974 | Ao | 502/527 X |
| 3,843,341 | 10/1974 | Hammel et al. | 65/22 |
| 3,848,033 | 11/1974 | Callahan et al. | 264/13 |
| 3,869,410 | 4/1975 | Bunda et al. | 252/455 R |
| 3,893,952 | 7/1975 | Ryska et al. | 253/477 R |
| 3,945,945 | 3/1976 | Kiovsky et al. | 252/463 |
| 3,957,627 | 5/1976 | Herrington et al. | 208/216 |
| 3,966,639 | 6/1976 | Callahan et al. | 252/439 |
| 3,972,990 | 8/1976 | Vesely | 423/628 |
| 3,978,269 | 8/1976 | Martin | 428/403 |
| 4,039,480 | 8/1977 | Watson et al. | 252/455 R |
| 4,059,423 | 11/1977 | DeVos et al. | 65/21 |
| 4,077,908 | 3/1978 | Stenzel et al. | 252/455 R |
| 4,111,713 | 9/1978 | Beck | 106/288 B |
| 4,153,539 | 5/1979 | Herrington et al. | 208/216 R |
| 4,214,020 | 7/1980 | Ward et al. | 427/296 |
| 4,222,977 | 9/1980 | Dobo | 264/63 |
| 4,230,463 | 10/1980 | Henis et al. | 55/16 |
| 4,257,798 | 3/1981 | Hendricks et al. | 65/21.4 |
| 4,260,524 | 4/1981 | Yamada et al. | 252/463 |
| 4,268,278 | 5/1981 | Dobo et al. | 55/16 |
| 4,279,632 | 7/1981 | Frosch et al. | 65/21.4 |
| 4,303,431 | 12/1981 | Torobin | 65/21.4 |
| 4,303,603 | 12/1981 | Torobin | 264/69 |
| 4,303,732 | 12/1981 | Torobin | 428/333 |
| 4,303,736 | 12/1981 | Torobin | 428/403 |
| 4,329,157 | 5/1982 | Dobo et al. | 55/16 |
| 4,342,643 | 8/1982 | Kyan | 208/134 |
| 4,344,787 | 8/1982 | Beggs | 65/21.4 |
| 4,348,458 | 9/1982 | Otstot | 428/366 |
| 4,390,456 | 6/1983 | Sanchez et al. | 252/448 |
| 4,415,512 | 11/1983 | Torobin | 264/9 |
| 4,548,912 | 10/1985 | Hettinger et al. | 502/527 X |

HOLLOW POROUS MICROSPHERES AS SUBSTRATES AND CONTAINERS FOR CATALYSTS AND METHOD OF MAKING SAME

PRIOR APPLICATIONS

The present application is a continuation-in-part of my copending application Ser. No. 639,126 filed Aug. 9, 1984 and my copending application Ser. No. 657,090 filed Oct 3, 1984. The application Ser. No. 639,126 is a continuation-in-part of application Ser. No. 429,923 filed Sept. 30, 1982, which application is a continuation of application Ser. No. 103,113 filed Dec. 13, 1979, which is a divisional of application Ser. No. 059,296 filed July 20, 1979, which is a continuation-in-part of application Ser. Nos. 937,123 and 944,643 filed Aug. 28, 1978 and Sept. 21, 1978, respectively.

The application Ser. No. 428,923 is now U.S. Pat. No. 4,548,196. The Ser. Nos. 103,113, 059,296, 937,123 and 944,643 are now abandoned.

BACKGROUND OF THE INVENTION

Field of the Invention

The invention relates to novel hollow porous microspheres used as substrates for catalyst and used as containers for catalyst to carry out a wide variety of catalyst reactions.

SUMMARY OF THE INVENTION

The present invention relates to microsphere catalysts made from hollow porous microspheres where the hollow porous microspheres are used as substrates and containers for catalysts.

The term microsphere catalyst as used herein is broadly defined to include a hollow porous microsphere which has been treated to coat or impregnate the walls of the microsphere with a catalyst or a catalyst and a catalyst support, or which has encapsulated or contained within the hollow central cavity of the microsphere a catalyst and/or catalyst support.

The hollow porous microspheres used as substrates and/or containers in accordance with the present invention are substantially spherical in shape, have substantially uniform diameters and have substantially uniform wall thickness and a single central cavity. The microspheres have interconnecting voids in the walls of the microspheres which result in the porous characteristics of the microspheres. The microspheres have uniform size and shape, uniform diameters, uniform wall thickness, uniform void content and uniform distribution of voids in the walls and high strength.

The walls of the hollow porous microspheres are free of latent solid or liquid blowing gas materials, and are substantially free of relatively thinned wall portions or sections and bubbles.

The hollow porous microspheres can be made from ceramic, glass, metal, metal glass and plastic particles, and mixtures thereof. The materials from which the microspheres are made can be selected to have catalytic activity as well as to provide good substrates for catalyst deposited on or contained in the hollow microspheres.

The microsphere catalyst of the present invention can be prepared by the below procedures.

(a) The microsphere catalyst can be prepared by coating or impregnating the hollow porous microspheres with a catalyst.

(b) The microsphere catalyst can be prepared by applying a catalyst support to hollow porous microspheres and then coating or impregnating the microspheres and catalyst support with the catalyst.

(c) The microsphere catalyst can be prepared by filling the microspheres with catalyst or catalyst and catalyst support.

(d) The microsphere catalyst can be prepared by coating or impregnating a support with a catalyst and filling the microspheres with the catalyst coated on the support.

The hollow porous microspheres of the present invention can be employed to encapsulate liquids, slurries or sol dispersions of catalyst, catalyst supports or catalyst precursors which can be caused to be deposited in the central cavity of the microspheres by hydrostatic pressure, by suction, or by centrifugation.

The microsphere catalyst prepared by the above procedures can be treated to immobilize the catalyst contained in the microsphere.

The immobilizing means can be a selective membrane which reduces the pore size of the hollow porous microspheres, such that the catalyst contained within the microsphere is prevented from escaping from the microsphere through the pores and entrance means, while only specific liquids, gases and/or organic molecules of predetermined molecular size can enter or leave the microsphere through the selective membrane.

The microsphere catalyst prepared by the above procedures can be treated to coat or impregnate the microsphere walls with an inorganic selective membrane or for low temperature reactions an organic selective semipermeable membrane to protect the catalyst and to provide a means to carry out selective chemical reactions.

The selective membrane can be used to protect the catalyst from damage or contamination. The selective membrane can also be used to control the selectivity of the catalyst reaction and thereby, for example, combine the processes of membrane selection and separation and catalytic activity.

The present invention also relates to methods for coating or impregnating and/or filling hollow porous microspheres with catalyst and/or catalyst supports to prepare improved microsphere catalysts. The hollow porous microspheres can be used as substrates or containers for a wide variety of catalyst and catalyst supports.

The porous wall of the hollow microsphere include entrance means through which catalyst and/or catalyst supports are introduced into the hollow interior or single central cavity of the microsphere. The porous wall can subsequently be treated to include means for immobilizing the catalyst within the hollow interior of the microsphere.

In an embodiment of the invention catalyst is introduced into the single central cavity of the microsphere. According to this embodiment, hollow porous microspheres each having entrance means in its porous wall which entrance means are large enough for the catalyst to pass through into the hollow interior are used. A slurry is brought into contact with the microspheres and sufficient pressure is applied for the slurry to pass through the entrance means into the hollow interior of the microsphere.

The term entrance means a used herein include microsphere pores, macro pores and micro pores. The microsphere pores, i.e. the interconnecting voids in the walls of the microspheres, are those obtained during formation of the microspheres and sintering of the dispersed particle compositions. The macro pores are those obtained by melting, vaporizing or decomposing macro particles contained in the walls of the microspheres. The micro pores are those obtained by treating the microspheres with a sol dispersion or sol gel to deposit the sol dispersion or sol gel in the microsphere pores and/or macro pores and heating to elevated temperatures to form from the sol dispersion or sol gel the micro pores in the interconnecting voids and macro pores in the microsphere walls.

The microsphere catalyst can be used to carry out a wide variety of catalyst reactions. The term catalyst reactions is defined as any chemical reaction carried out effected by a catalyst. The term catalyst reactions includes petroleum refining processes, chemical processes and emission control processes. The term catalyst reaction is to be given as broad a meaning as possible consistent with the requirement that it involves the use of at least one reactant which is modified, converted, altered, or otherwise reacted, more or less specifically, through the assistance of the catalyst in order to manufacture or modify a particular substance. Thus, catalyst reactions encompass such diverse technologies as petroleum refining process, e.g. catalytic cracking, alkylation, hydrotreating, hydrocracking and catalytic reforming; chemical processes, e.g. polymerization, organic synthesis, ammoxidation, oxidation and oxchlorination, ammonia and methanol synthesis; and emission control, e.g. automobile emission control and emission control of effluents from incinerators, power generation plants, ovens, wood stoves and acid plants. The term catalyst reactions, as used herein, is intended to exclude the biotech reactions, e.g. biological processes disclosed and claimed in applicant's copending application Ser. No. 657,090 filed Oct. 3, 1984.

PRIOR ART

In recent years, there have been many attempts to improve catalyst properties by using hollow porous microspheres as catalyst substrates and as containers for catalyst. Though there are known methods for producing hollow microspheres the known methods suffer one or more shortcomings including producing very small microspheres, microspheres of random wall size and diameter distribution, microspheres which contain latent liquid, solid or gas blowing agents, and microspheres which have thin wall sections or walls having small gas bubbles dissolved or trapped in the walls. See, for example, Sowman U.S. Pat. No. 4,349,456 (sol gel process), and De Vos et al U.S. Pat. No. 4,059,423 (latent blowing gas process). The shortcomings present in the prior art microspheres made it difficult to obtain microspheres of the desired porosity and strength and to obtain catalyst of controlled and predictable activity and made it difficult to control the desired catalyst reactions.

Prior to the time applicant made the present invention there was no known simple economical method of producing for use as catalyst substrate or containers for catalyst relatively large porous microspheres where the microspheres were substantially spherical, of substantially uniform diameter, uniform wall thickness, uniform void content and uniform void distribution and intercommunication of the voids in the walls and uniform strength and where the microsphres could be produced at about ambient temperatures. Prior to the time applicant made the present invention there was no ready means for encapsulating catalyst, e.g. solid particulate catalyst in a rigid hollow microsphere or means for immobilizing catalyst in a rigid hollow microsphere, e.g. by use of an immobilizing membrane.

Further, the conventionally produced catalyst, e.g. catalyst with binders, catalyst without binders and molecular sieve catalyst tend during use to attrite with the formation of small particles and/or fines. The small particles and/or fines in some reactions elutriate and are loss to the reaction and may cause pollution problems and/or contamination of the desired products. The small particles formed by attrition or the particles that are the small particles of wide or narrow particle size distribution of catalyst, tend to cause packing in a catalyst bed. The packing of the catalyst bed can cause an increase pressure drop across the catalyst bed and can cause channeling of the reactant in the catalyst bed which results in reduced contact between the catalyst and reactant.

Where binder materials are required to bind the catalyst particles to form the desired size and shape of catalyst pellet, the binder tends to reduce the diffusion rate at which the reactant can reach the catalyst and reduces the rate of the reaction. The use of binders also reduces the surface area of the catalyst available to the reactant.

OBJECTS OF THE INVENTION

It is an object of the present invention to provide improved microsphere catalysts using hollow porous microspheres as catalyst substrates and containers for catalysts.

It is another object of the invention to prepare microsphere catalysts from hollow porous microspheres, which microspheres have a single central cavity, have substantially uniform diameters and substantially uniform wall thickness, where the walls of the microspheres have substantially uniform void content and substantially uniform distribution of interconnecting voids.

It is another object of the invention to prepare microsphere catalysts by coating or impregnating hollow porous microspheres with a catalyst or by applying a catalyst support to the microspheres and then coating or impregnating the microspheres and catalyst support with a catalyst.

It is another object of the invention to prepare microsphere catalysts by filling the hollow porous microspheres with a catalyst or with a catalyst and catalyst support.

It is another object of the invention to immobilize the catalyst contained in the microspheres by treating the microspheres containing the catalyst to agglomerate the catalysts to a sufficiently large size such that the catalysts do not flow out of the catalyst entrance means.

It is another object of the invention to immobilize the catalyst contained in the microspheres by treating the microspheres containing the catalyst to provide the microspheres with an inorganic or organic membrane such that the catalyst is immobilized and protected.

It is another object of the invention to provide the microsphere catalysts with an inorganic selective membrane or an organic selective membrane such that selective chemical reactions can be carried out.

It is another object of the invention to provide structural support for catalysts without significantly diminishing the diffusion rates of reactant gases or liquids through the microsphere substrate or microsphere container and into and out of contact with the catalysts such that high reaction rates can be obtained and maintained.

It is another object of the present invention to provide extremely finely divided substrates within the microspheres for deposition of catalyst, which substrates would be too weak in a reactor environment.

It is another object of the present invention to allow extremely small size catalyst particles contained within the microspheres to be used in a reactor environment which otherwise would elutriate and carry away such small catalyst particles.

It is another object of the present invention to provide microsphere catalyst for carrying out a wide variety of catalyst reactions.

It is another object of the invention to provide microsphere catalysts for use in fixed bed, moving bed, fluidized bed, batch, continuous or semi-continuous catalyst reactions.

These and other objects of the invention will become apparent as the description proceeds.

BRIEF DESCRIPTION OF THE DRAWINGS

The attached drawings and photographs illustrate exemplary forms of the present invention for making microsphere catalysts from hollow porous microspheres and illustrate hollow microsphere catalysts that are obtained.

The FIG. 1 of the drawings is an enlarged cross-sectional view of a hollow porous microsphere useful as a catalyst substrate and catalyst container.

Figure 1:
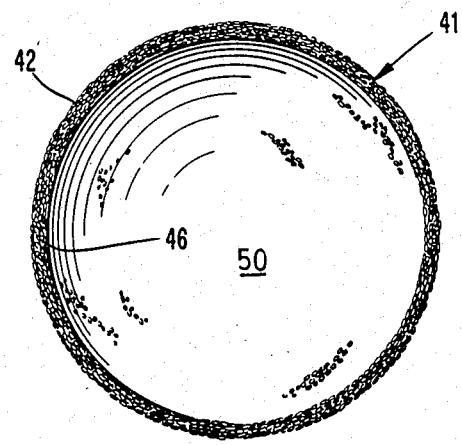
Figure 2:
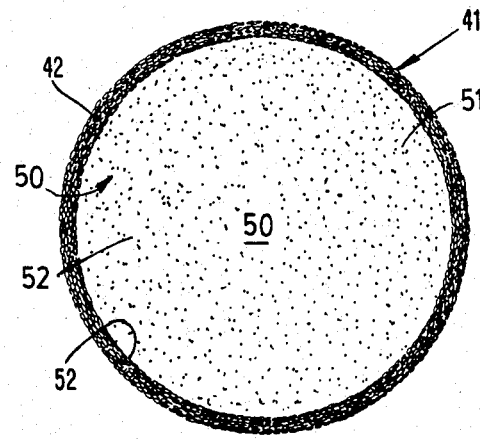

The FIG. 2 is a cross-sectional view of the microsphere similar to FIG. 1 showing catalyst deposited on the inner wall surface of the microsphere wall.

Figure 3:
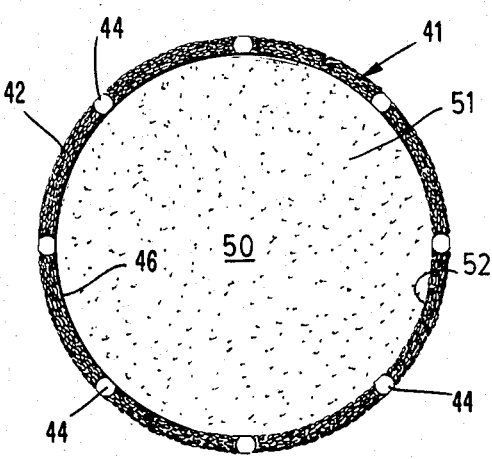

The FIG. 3 of the drawings is an enlarged cross-sectional view of a hollow porous microsphere including a multiplicity of macro pores extending through the microsphere walls and showing catalyst deposited on the inner wall surface of the microsphere wall.

Figure 4:
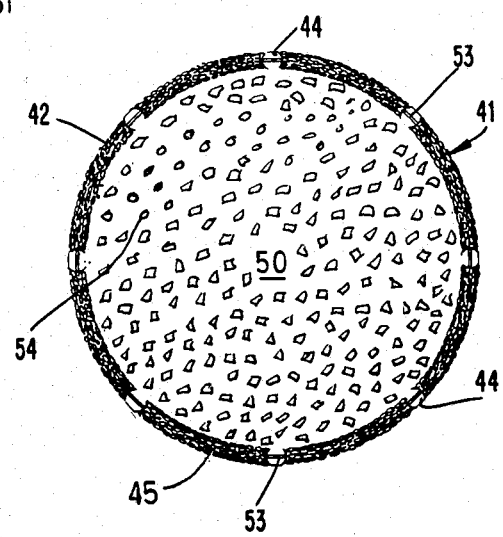

The FIG. 4 is a cross-sectional view of the microsphere similar to FIG. 3 showing the single central cavity filled with catalyst and the macro pores sealed with a selective membrane.

Figure 5:
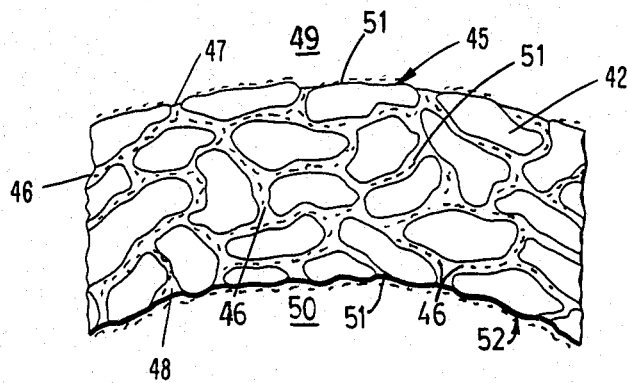

The FIG. 5 is an enlarged cross-sectional view of a section of the wall of a hollow microsphere of FIG. 2 which has been impregnated with a catalyst solution and heated to remove the liquid phase of the solution and to deposit catalyst on the inner and outer wall surfaces and in the inner connecting voids in the wall.

Figure 6:
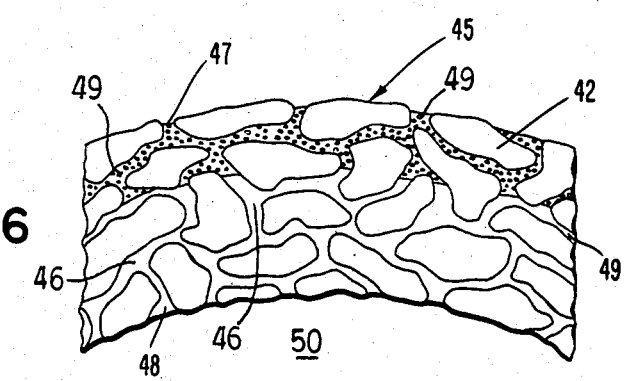

The FIG. 6 is a cross-sectional view of a section of the wall of a microsphere similar to FIG. 5 which has been treated with a sol dispersion and again heated at elevated temperature to deposit solid particles from the sol dispersion. The solid particles form a lattice work of the particles in the inner connecting voids in the wall to reduce the pore size, i.e., to produce micro pores, which micro pores can provide support for a catalyst to be deposited on or impregnated in or otherwise placed in the micro pores or which can form an inorganic selective membrane.

Figure 7:
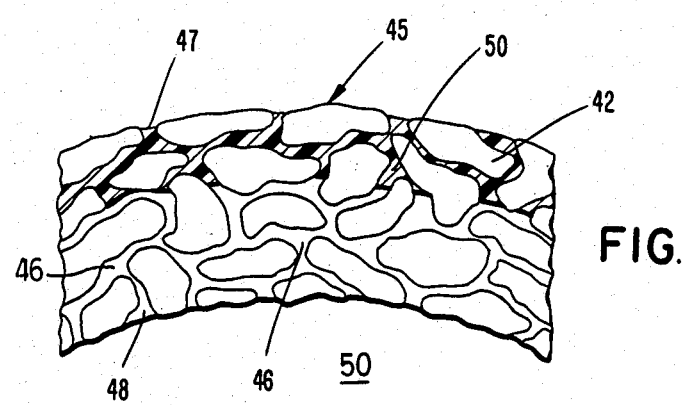

The FIG. 7 is a cross-sectional view of a section of the wall of a microsphere similar to FIG. 5 in which the pores in the wall of the hollow microsphere have been sealed with an organic selective semipermeable membrane to protect a contained catalyst and to make the catalytic reaction selective.

Figure 8:
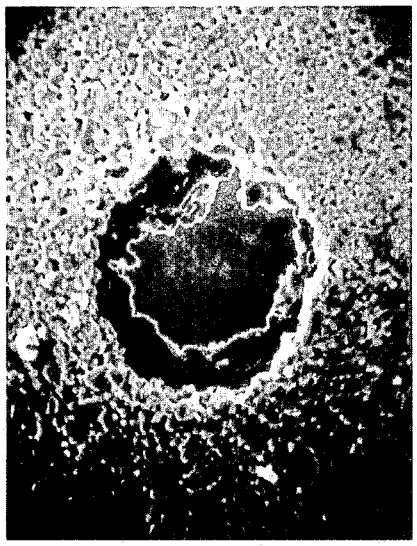

The FIG. 8 is a microphotograph (900×) of a top view of a portion of a microsphere wall similar to FIG. 3 showing a macro pore therein.

Figure 9:
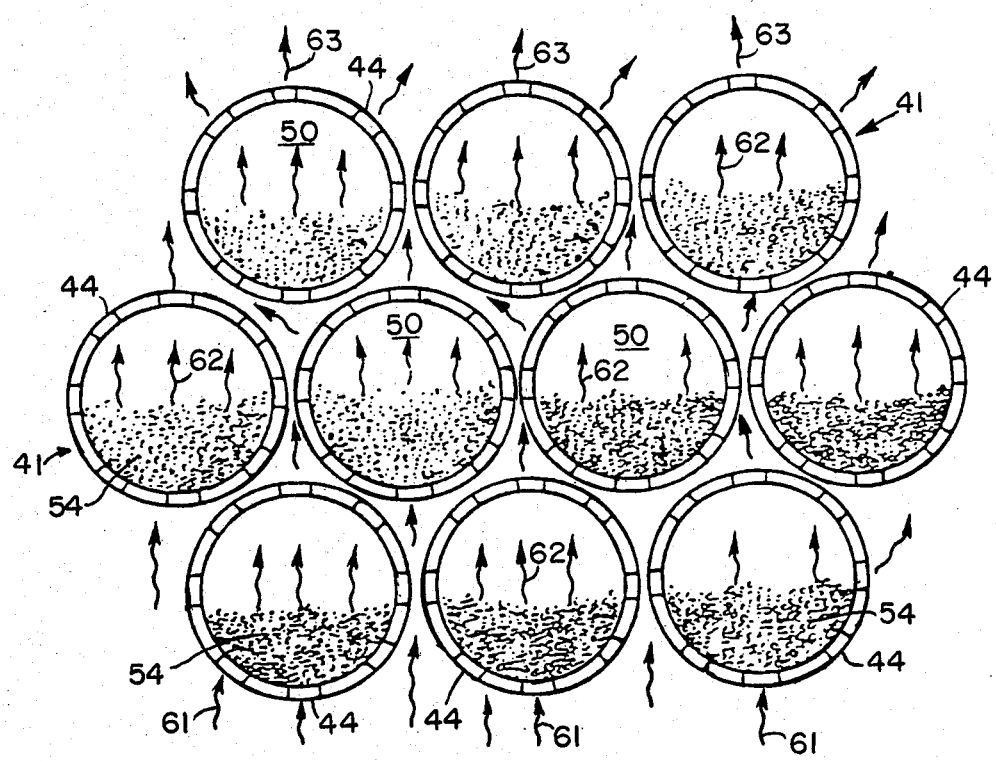

The FIG. 9 is a schematic illustration of a bed of microspheres which have macro pores and which are partially filled with a finely divided catalyst.

Figure 10:

FIG. 10 is a photograph (900×) showing a section of the thin wall and a section of the inner wall surface of an alumina particle microsphere on which inner wall surface there has been deposited finely divided catalyst.

Figure 11:

FIG. 11 is a photograph (900×) showing a cross section of the thin wall and the inner wall surface of a section of an alumina particle microsphere.

THE ADVANTAGES

The present invention overcomes many of the problems associated with prior attempts to produce catalysts from hollow microspheres. The present invention allows the production of improved microsphere catalysts from rigid hollow porous microspheres, wherein the microspheres have predetermined characteristics of uniform diameter, uniform wall thickness and uniform void content, uniform void distribution and void intercommunication in the walls and high strength such that hollow porous microsphere catalysts can be designed, manufactured and tailor made to suit a particular desired process use. The diameter, wall thickness, void content, void distribution and void intercommunication in the walls, strength and catalytic properties of the hollow porous microspheres can be determined by carefully selecting the catalysts, catalyst supports, the constituents of the dispersed particle composition, particularly the dispersed solid particles, the size of the dispersed solid particles and the volume percent solids of the dispersed particles, i.e., liquid/solids, composition.

The present invention allows a wide range of selection of particles to form the hollow porous microspheres and a wide range of selection of catalysts and catalyst supports to form the microsphere catalysts.

The present invention provides a practical and economical means by which catalysts can be made using hollow porous microspheres having uniform diameters and uniform thin walls of high strength as the catalyst substrates and/or a containers for the catalysts. The present invention allows rapid encapsulation, i.e. filling of the microspheres with relatively large particle size catalysts through macro pore entrance means. The present invention provides for the production of catalysts from hollow porous microspheres at economical prices and in large quantities.

The present invention, as compared to the prior art process (De Vos U.S. Pat. No. 4,059,423) for producing a hollow microspheres using a latent liquid or solid blowing agent to produce the hollow microspheres, produces catalyst from uniform size spheres as compared to spheres of random wall size and diameter distribution, and produces catalysts from microspheres the walls of which are of uniform thickness, are free of thin walled portions, trapped bubbles or gases, or trapped latent blowing agents which weaken the microsphere walls.

The present invention, as compared to the prior art sol gel microcapsule process (Sowman U.S. Pat. No. 4,349,456), produces large uniform size spheres for use as catalyst substrates and catalyst containers with uniform thin walls. The Sowman sol gel process produces small spheres which are of random size distribution and which spheres have thin and weakened wall portions.

An additional advantage of the microsphere catalysts of the present invention is that the catalysts do not require a binder material and are no longer diffusion limited by the effect of the binder.

A further advantage of the microsphere catalysts of the present invention is that the pressure drop across a catalyst bed is substantially reduced by the avoidance of attrition formation of small catalyst particles and packing of the catalyst bed.

A still further advantage of the microsphere catalysts of the present invention is that improved catalyst-reactant contact is maintained by the avoidance of channeling of the reactant.

The microsphere catalysts can provide high flux rates of reactants, while still providing greater overall strength. The microsphere catalysts of the present invention in some applications can withstand two point pressures up to at least about 200 psia, for example, 500 psia. In view of the high wall strength, the microsphere catalysts are much more easily handleable and transferrable and can be used in fixed bed processes at high packing densities, for example, bed heights of up to 30 feet or more, in moving bed processes, and in fluidized bed processes wherein the microsphere to microsphere contact and microsphere to reactor wall contact impacts do not cause structural damage to the microsphere or to the catalyst. Further, the generally low density and mass of the microsphere catalysts contributes to this advantage and also reduces the shear and impact forces which could be harmful to the microsphere catalysts.

Because of the relatively low cost of the microspheres the catalyst can be discarded periodically for short life time catalyst. The microsphere catalyst can also be recycled for regeneration of the catalyst.

In addition, the microspheres of the present invention are more uniform in wall size and diameter size than the prior art microspheres. Further, a much wider range of diameters and wall thicknesses are available for the microspheres than those used in the conventional catalyst processes. Therefore, control of process parameters, e.g. mass flow rates, fluid dynamics, heat transfer, etc., is greatly simplified.

Because the microspheres are hollow and have porous walls, they will generally have bulk densities which are significantly lower than the density of the solid particles forming the microsphere walls. The microspheres when filled with catalyst can approximate the density of the liquid reaction mediums used in some catalyst processes. The microspheres, i.e. microsphere catalysts, can accordingly be more easily suspended in liquid reaction mediums or other liquid mediums, e.g. a waste stream, etc., used in the catalyst process. Further, because of the microsphere catalysts relatively low densities they are also more easily suspended in vapor phase or gaseous reaction mediums.

The relatively low densities of the microsphere catalysts of the present invention provide the highly important advantages of: less mechanical energy is required to mix or stir suspensions of the microsphere catalysts in catalytic reactions thereby lower overall costs for carrying out the reactions. The lower microsphere catalysts densities reduces the impact forces or collision pressures of particle-to-particle, i.e. microsphere catalyst-to-microsphere catalyst, collisions, thereby reducing the likelihood of damage to the catalysts and/or to the microsphere walls, and reducing the likelihood of damage or shearing stresses to immobilizing means or selective membranes. In addition, the low microsphere catalyst densities reduces the time required to heat the catalyst to operating temperatures.

Still, another advantage of the microsphere catalysts of this invention is that the microsphere containers, while non-deformable under conditions of use in the catalyst reaction processes, can be broken where necessary or desired for recovery of the catalysts.

Additional advantages occur in the microsphere catalysts where the processes are inhibited by intracrystalline or intercrystalline diffusional resistance, elutriation of fine particles, and problems of gross handling and efficiency of contacting.

A variation, in which colloidal micro-solids are used to partially block the regular microsphere pores, allows increased catalyst surface area and a protective selective membrane for the contained catalyst.

An added advantage of the present invention is the preparation of binderless pellets, with or without a protective inorganic or organic selective permeable membranes.

These and other advantages of the present invention will become evident by the description of the invention that follows.

DETAILED DISCUSSION OF THE DRAWINGS

The invention will be described with reference to the accompanying Figures of the drawings wherein like numbers designate like parts throughout the several views.

FIG. 1 of the drawings is an enlarged cross-sectional view of a hollow porous microsphere 41 used as a catalyst substrate or catalyst container in accordance with the present invention. The microsphere illustrated shows dispersed particles 42, interconnecting voids 46 (see also FIG. 5) and a single central cavity 50.

The FIG. 2 is a cross-sectional view of the microsphere similar to FIG. 1 showing catalyst 51 deposited on the inner wall surface 52 of the microsphere wall. The catalyst can be deposited from a solution containing the catalyst or by impregnation of the hollow microsphere with the solution and drying to deposit the catalyst. The catalyst 51 is also deposited in the interconnecting voids or channels 46, and on the outer surface of the microsphere wall. The catalyst in the interconnecting voids and on the outer wall surface are not shown, see however FIG. 5 below.

The FIG. 3 of the drawings is an enlarged cross-sectional view of a hollow porous microspheres 41 including a multiplicity of macro pores 44 of a predetermined size extending through the microsphere wall and showing catalyst 51 deposited on the inner wall surface 52 of the microsphere wall. The FIG. 3 also shows dispersed particles 42 and interconnecting voids 46. The catalyst 51 can be deposited from a solution containing the catalyst or by impregnation of the hollow microsphere with the solution and drying to deposit the catalyst. The catalyst 51 is also deposited in the interconnecting voids or channels 46, and on the outer surface of the microsphere wall. The catalyst in the interconnecting voids 46 and outer wall surface, as in FIG. 2, are not shown, see however FIG. 5 below. The macro pores 44 allow easy communication of the reactant into and out of the single central cavity 50 of the microsphere such that efficient contact of the reactant with the catalyst is achieved.

The FIG. 4 is a cross-sectional view of the microsphere similar to FIG. 3 showing the single central cavity 50 filled with a solid particulate catalyst 54 and showing macro pores 44 that are sealed with an inorganic permeable membrane 53. The FIG. 4 of the drawing shows macro pore 44 entrance means, e.g. openings or passageways of larger dimensions than the largest microsphere pores 46, 47 and 48 (FIG. 5), that are provided to ensure that the catalyst 54 suspended, e.g. in a slurry or sol dispersion will readily pass through the entrance means 44 which extend through the wall 45 of the microsphere 41 into the hollow central cavity 50 of the microsphere. The relatively large macro pore entrance means in the walls of the microsphere, are at least twice as large as the maximum microsphere pore size and preferably at least twice as large as the catalyst particles 54. The term entrance means broadly includes the microsphere pores, the interconnecting voids and the macro pores. However, even with small dimensioned catalyst particles, it is preferred to include macropores 44 in the microsphere wall to facilitate the expedite the process of encapsulating the catalyst or filling the microspheres with catalyst and to allow good access of the reactants to the catalyst contained in the microspheres.

The FIGS. 5, 6 and 7 show enlarged detailed cross-sectional views 45 of a section of the wall of a hollow porous microsphere similar to FIG. 2 or 3 used in accordance with the present invention to make an improved catalyst. The FIGS. 5, 6 and 7 show pores 47 at the outer wall surface of the microsphere which pores extend by interconnecting voids 46 through the wall 45 of the microsphere to the inner wall surface pore 48 of the microsphere.

As can be seen from FIGS. 5, 6 and 7 the sintered together particles 42 forming the solid porous wall 45 of the microsphere 41 define, within the wall, interconnecting voids or channels 46. For simplicity of illustration, the particle-to-particle contact of the sintered together particles is not shown. The interconnecting voids 46 are continuous and extend, from the pore opening 47 at the outer wall surface to the pore or opening 48 at the inner wall surface. The interconnecting voids 46 provide paths or passageways for transporting gases, liquids and very finely divided, e.g. submicron, dispersed particles from the exterior of the microsphere to the interior single central cavity 50 of the microsphere 41.

The FIG. 5 is an enlarged cross-sectional view of a section of the wall of a hollow microsphere of FIG. 2 or 3 which has been impregnated with a catalyst solution and heated to remove the liquid phase of the solution and to deposit catalyst on the inner and outer wall surfaces and in the inner connecting voids 46 in the wall. The FIG. 5 shows catalyst 51 deposited on the outer wall surface 45 of the microsphere, on the walls or surfaces of the interconnecting voids 46 and on the inner wall surface 52 of the microsphere.

The FIG. 6 is a cross-sectional view of a section of the wall of a microsphere similar to FIG. 5 which has been treated with a sol dispersion and heated at elevated temperature to deposit solid particles from the sol dispersion. The microspheres can be treated with a sol dispersion or a sol gel, e.g., an alumina or silica sol gel, or other dispersions of charged or uncharged colloidal particles and heated at elevated temperature to deposit in the interconnecting voids 46 and on the surfaces of the particles that form the interconnecting voids of the microsphere wall small solid particles 49, e.g., alumina or silica particles. The deposited alumina or silica particles can form a catalyst support and/or an immobilizing or a selective membrane. The sol dispersion or sol gel composition can be deposited in a layer in the outer portion of the microsphere wall, in the center portion, in the inner portion of the microsphere wall or throughout the microsphere wall. The solid particles from the sol dispersion or sol gel are deposited and adhere to the surfaces of the particles that form the interconnecting voids 46, and the solid particles from the sol dispersion link-up and form in the interconnecting voids a porous lattice work of linked-up deposited sol or sol gel particles.

The porous lattice work of solid particles from, e.g., the sol dispersion or sol gel deposited in the interconnecting voids and on the surface of the particles that form the voids 46 serves to reduce the void content, i.e., the volume percent voids and the pore size of the voids in the microsphere wall, i.e., form micro pores, when a controlled smaller pore size is desired. The reduction of the pore size and the void content at the same time increase the surface area of support in the pores in those embodiments in which it is desired to deposit, impregnate or otherwise place a catalyst in the interconnecting voids and/or on the outer pore area of the microsphere wall.

In a preferred embodiment of the invention, the catalyst or a selective membrane is impregnated or deposited within the microsphere wall to strengthen the adhesion of the catalyst or selective membrane to the hollow microsphere wall and avoid lifting off of the catalyst and/or selective membrane during catalytic processes or regeneration cycles.

The FIG. 7 is a cross-sectional view of a section of the wall of a microsphere similar to FIG. 5 in which the pores in the wall of the hollow microsphere have been impregnated and sealed with an organic selective semipermeable membrane 50 to protect a contained catalyst and to make the catalytic reaction selective. The organic semipermeable membrane 50 is impregnated, deposited on otherwise placed in the microsphere wall through surface pores 57 and into voids or interconnecting channels 46, closing pores 47 and forming a discontinuous thin film 50 in the wall of the hollow microsphere.

The FIG. 8 is a micro photograph (900× magnification) of a top view of a portion of the microsphere wall showing a macro pore therein. The FIG. 8 shows a top view of a portion of a microsphere wall 40 micron thick after decomposition of an acrylic macro particle of about 50 microns diameter. The sintered solid particles forming the microsphere wall are alumina ($Al_2O_3$) particles having a particle size of about 1 to 3 microns. The microsphere is about 4000 microns in diameter and is made from alumina particles.

As can be seen from the micro photograph of FIG. 8, the perimeter of the macro pore is generally free of sharp or jagged protrusions which could result from extension into the macro pore of portions of one or more of the finely divided solid wall-forming particles since any such sharp or jagged protruding solid particles will tend to be smoothed by the subsequent sintering step. However, it is possible to even further smoothen the surface of the macro pore by using as the macro particles a material, such as glass and metals, which at least partially soften and melt, rather than decompose, at the operating temperature. In such case, when the microsphere is heated, at least a portion of the macro particle will diffuse and penetrate into and between the dispersed solid particles surrounding and coating the macro particle thereby assuring leaving behind a smooth macro pore surface (periphery). Furthermore, it is possible to select mutually reactive materials for the finely divided solid particles and the macro particles, for example, alumina solid particles and glass macro particles, which will react to form alumina silicate, at or below the sintering temperature, thereby further strengthening, as well as smoothing, the macro pore surface.

The FIG. 9 of the drawings is a schematic illustration of a bed of microspheres 41 which have macro pores 44 and which are partially filled with a finely divided catalyst 54. Gas or liquid feed reactant medium 61 enter microspheres 41 through macro pores 44, contact catalyst 54 in central cavity 50 and react to form the desired product and by-products 62. The product and by-products together with any unreacted feed 63 exit the central cavity 50 by way of macro pores 54 to go to further processing. Each microsphere 41 with its catalyst 54 and central cavity 50 comprises an individual small reactor.

The FIG. 10 is a photograph (900×) showing a section of the thin wall and a section of the inner wall surface of a hollow porous alumina particle microsphere and showing finely divided silica catalyst deposited on the inner wall surface of the microsphere wall. The silica catalyst was deposited from an aqueous sol consisting of colloidal silica. The microsphere was placed in the sol until saturated with the sol, dried and then heated to deposit the catalyst. The microsphere has a diameter of 2400 microns and a wall thickness of 30 microns.

The FIG. 11 is a photograph (900×) showing a cross section of the thin wall and the inner wall surface of a hollow porous microsphere made from alumina particles. The microsphere is about 3000 microns in diameter and has a wall thickness of 25 microns and 40% void content in the wall.

DESCRIPTION OF HOLLOW POROUS MICROSPHERES

The hollow porous microspheres provide uniformly sized substrates and uniformly sized containers for catalysts. The method for the manufacture of the microspheres and their physical properties and dimensions are disclosed in and are the subject matter of applicant's copending application Ser. No. 639,126 "Hollow Porous Microspheres and Method and Apparatus for Producing Them", filed on Aug. 9, 1984. The entire disclosure of the copending application is incorporated herein in its entirety by reference thereto.

The hollow porous microspheres of the present invention can be made from dispersed particle compositions which comprise dispersed particles, a binder, a film stabilizing agent, a dispersing agent and a continuous liquid phase.

The hollow porous microspheres are made from aqueous or non-aqueous suspensions or dispersions of finely divided inorganic or organic solid particles, particularly ceramic, glass, metal, metal glass and plastic particles, a binder material, a film stabilizing agent, a dispersing agent for the solid particles, and a continuous aqueous or non-aqueous liquid phase. The suspension or dispersion is blown into microspheres using a coaxial blowing nozzle, the microspheres are heated to evaporate the solvent and further heated or cooled to harden the microspheres. The hardened microspheres are then subjected to elevated temperatures to decompose and remove the binder and any residual solvent or low boiling or melting material. The resulting hollow porous microspheres are then fired at further elevated temperatures to cause the particles to sinter and/or fuse at the points of contact of the particles with each other such that the particles coalesce to form a strong rigid network (lattice structure) of the sintered-together particles.

As described in the copending application Ser. No. 639,126, macro pores can be obtained by incorporating in the solid particle suspension or dispersion, prior to the blowing step, a small percentage of decomposable particles (macro particles) having a diameter greater than the maximum dimension of the microsphere wall, for example, about 1 to 1000 microns, preferably 5 to 400 microns, more preferably about 10 to 100 microns, especially preferably about 20 to 100 microns. These decomposable macroparticles are confined along with the smaller dispersed solid particles in the wall of the microsphere. However, the decomposable macro particles are decomposed at the step of decomposing the organic binder or at the subsequent step of sintering the dispersed particles depending on the decomposition temperature of the decomposable macro particles, leaving behind large openings (macro pores), such as shown in FIG. 3. In addition, metal and glass beads or pellets having a melting temperature below the sintering temperature, preferably at least 100° C. below the sintering temperature can also be used.

Generally, the material of the dispersed solid particles forming the walls of the microspheres is not particularly critical so long as it is compatible with and non-contaminating to the catalyst and not detrimental to the process, and the ceramic particles, glass particles, metal particles, metal glass particles, and plastic particles disclosed in the aforementioned patent application Ser. No. 639,126 can be used.

On the other hand, it is often preferred or desirable in certain catalytic reactions for the catalyst to be deposited and adhered to a substrate (in the case of the present invention, the substrate being the inner wall surface of the hollow microsphere, and the walls of the interconnecting voids). In such cases, therefore, the material of the dispersed particles will be selected based on its ability to provide a surface to which the catalyst can be deposited and adhere by physical and/or chemical bonding. Many materials will naturally meet this requirement, although to differing degrees. Furthermore, it is also known in the art to provide chemical treatment to substrates to increase their ability to bond to specific catalysts.

The hollow porous microspheres are free of any latent solid or liquid blowing gas materials or latent blowing gases. The walls of the hollow microspheres are free or substantially free of any relatively thinned wall portions or sections, trapped gas bubbles, or sufficient amounts of dissolved gases to form bubbles.

The term "latent" as applied to latent solid or liquid blowing gas materials or latent blowing gases is a recognized term of art. The term latent in this context refers to blowing agents that are present in or added to glass, metal and plastic particles. In the prior art processes the glass, metal and plastic particles containing the "latent blowing agent" are subsequently heated to vaporize and/or expand the latent blowing agent to blow or "puff" the glass, metal or plastic particles to form microspheres.

The hollow porous microspheres, because the walls are substantially free of any thinned sections, trapped gas bubbles, and/or sufficient amounts of dissolved gases to form trapped bubbles, are substantially stronger than the hollow microspheres heretofore produced.

The hollow porous microspheres contain a single central cavity, i.e., the single cavity is free of multiple wall or cellular structures. The walls of the hollow porous microspheres are free of bubbles, e.g., foam sections.

The hollow porous microspheres can be made in various diameters and wall thickness, depending upon the desired end use of the microspheres. The microspheres can have an outer diameter of 200 to 10,000 microns, preferably 500 to 6000 microns and more preferably 1000 to 4000 microns. The microspheres can have a wall thickness of 1.0 to 1000 microns, preferably 5.0 to 400 microns and more preferably 10 to 100 microns.

When the dispersed particles are sintered, the smaller particles can be dissolved into the larger particles. The sintered particles in the hollow porous microspheres can be generally regular in shape and have a size of 0.1 to 60 microns, preferrably 0.5 to 20 microns, and more preferrably 1 to 10 microns.

In a preferred embodiment the hollow porous microspheres can have diameters of 1200 to 6000 microns and wall thicknesses of 10 to 200 microns, and preferably diameters of 2000 to 4000 microns and wall thicknesses of 20 to 100 microns.

The porosity, diameter and wall thickness of the hollow porous microspheres will affect the average bulk density of the microspheres. The porous ceramic, glass, metal, metal glass and plastic microspheres prepared in accordance with the invention will have an average bulk density of 1 to 150 lb/ft$^3$, (0.020 to 2.4 gm/cc), preferably 2.0 to 60 lb/ft$^3$, (0.030 to 1.00 gm/cc), and more preferably 4 to 20 lb/ft$^3$, (0.060 to 0.32 gm/cc).

In certain embodiments of the invention, the ratio of the diameter to the wall thickness, and the conditions of firing and sintering the hollow microspheres can be selected can that the microspheres are flexible, i.e., can be deformed a slight degree under pressure without breaking.

The preferred embodiment of the invention, particularly with the ceramic materials, is to select the ratio of the diameter to wall thickness and the conditions of firing and sintering the hollow porous microspheres such that rigid hollow porous microspheres are obtained.

The fired hollow porous microspheres of the present invention can have a distinct advantage of being rigid, strong and capable of supporting a substantial amount of weight. They can thus be used to make simple inexpensive catalyst substrates and catalyst containers that can be load bearing systems for carrying out catalytic reactions.

The hollow porous microsphere containers of this invention, in addition to their uniformity in structure, have the highly advantageous characteristic of high mechanical strength due to the sintering together of the solid dispersed wall-forming particles. Due to this high mechanical strength, The microsphere resist damage under the conditions of actual use in catalytic raction processes. The microspheres have the ability to withstand the forces exerted by contact with other microspheres or the walls and surfaces of the process apparatus, as well as hydrostatic forces and pressures encountered in catalytic reaction processes, including fluidized bed, stacked bed, plug flow, and other types of catalytic reaction processes, without any significant deformation of shape and without breakage and, further, without imparting stress forces on the selective membrane or immobilizing means. Preferably the walls of the hollow porous microsphere containers are rigid and are capable of withstanding two point contact pressure of at least 30 psi (2.1 kg/cm$^2$), preferably from about 50 psi (35 kg/cm$^2$) to about 3000 (psi 211 kg/cm$^2$). As used herein "two point contact pressure" is measured with respect to a one-inch square tightly packed monolayer of the microspheres resting on a hard flat surface with a flat mass placed thereon. The weight of the mass causing breakage of one or more microspheres divided by one square inch is the "two point contact pressure."

The porosity or void content of the walls of the hollow microspheres is dependent upon the volume percent of dispersed solids of the entire dispersed particle composition and the firing and sintering temperature.

The porosity of the walls, i.e., the void content, of the hollow fired microspheres can be 5% to 45%, preferably 15% to 35% and more preferably 20% to 30% by volume of the microsphere wall.

In an embodiment of the invention the hollow microspheres can be substantially spherical and can have substantially uniform diameters or they can have thickened wall portions on opposite sides of the microspheres. The thickness of the thickened portions depends in part on the visocity of the dispersed particle composition, the rate of hardening, the distance away from the coaxial blowing nozzle when they harden and the ability of the surface tension properties of the dispersed particle composition to absorb and distribute in the wall of the microsphere the portions of the dispersed particle composition that would or may form filaments.

The preferred hollow microspheres are the substantially spherical microspheres. However, in some applications, for example, packed bed systems, the hollow microspheres with the thickened wall portions can also be used. The thickened wall portions, on the opposite sides of the microspheres, can be 1.01 to 2.0 times the microsphere wall thickness; can be 1.1 to 1.5 times the microsphere wall thickness; and can be 1.2 to 1.3 times the microsphere wall thickness. The cross-section of the microsphere other than at thickened wall portion section is substantially spherical and of substantially uniform wall thickness. All the microspheres produced under a given set of operating conditions and dispersed particle composition constituents are substantially the same in sphericity, wall thickness, void content and void distribution. A specific advantage of the use of the hollow porous microspheres of the present invention is that in the production of hollow microspheres, the preceeding and the following microspheres that are produced are substantially the same.

The hollow porous microspheres used to produce the microsphere catalyst in accordance with the present invention, depending in part on the dispersed particle size, e.g., 0.1 to 5.0 microns, and dispersed particle size distribution, volume percent solids used and firing temperatures, can contain interconnecting voids or channels between the sintered particles in which the distance between particles, can be, for example, 1 to 5 microns.

The microsphere pores and interconnecting voids or channels will, depending on the size of the dispersed particles and the particle size distribution of the dispersed particles and the porosity of the microsphere walls, can range from about 0.05 to 20 microns, generally from about 0.1 to 10 microns, and more generally from about 0.1 to 5 microns. For many catalyst materials having particle sizes of less than about 1–2 microns, the pore sizes or at least a substantial portion of the pores, will be sufficiently large to permit free passageway of these catalysts from the exterior to the interior of the microsphere. However, the pore size may be smaller than or only slightly larger (e.g. up to about 100% larger) than the maximum dimension of the catalyst material—this will generally be the case for many of the catalyst materials desired to be used. In this case, the microspheres containing macro pores can be used when it is desired to put the catalyst within the central cavity of the microspheres.

In applications in which a hollow porous microsphere is not needed or wanted and/or where it is desired to have maximum wall strength the heating at elevated temperatures can be carried out at temperatures high enough and for a time long enough to melt the dispersed particles, to fuse the pores closed, to fuse the interconnecting voids closed and to remove substantially all of the interconnecting void structure from the walls of the hollow microspheres. The heating at elevated temperatures is carried out at temperatures high and time long enough enough for the air or other gas in the interconnecting voids to dissolve in the fused dispersed particles or to form bubbles and migrate to the surfaces of the microspheres and out of the walls of the microspheres and to close off and seal the interconnecting void structure in the microsphere wall. The treatment step can be carried out in a manner so that it does not collapse the microsphere wall and the microspheres retain their spherical shape. In this embodiment the catalyst is deposited on the outer wall surface of the microsphere.

Alternatively, microspheres may be treated to have the interconnecting voids filled and sealed with a dispersion of colloidal size particles that have a lower melting temperature than the dispersed particles in the hollow porous microspheres and then heated to fuse the colloidal size particles to seal the interconnecting voids.

Without intending to be limiting but rather to be used as a point of reference, the Table I below provides exemplary relationships between the outer diameters of the microspheres, microsphere wall thickness, dispersed particle size, and ratio of the microsphere wall thickness to the outside diameter of the microsphere.

TABLE I

|  | Broad | Preferred | More Preferred |
|---|---|---|---|
| Diameter (microns) | 200 to 10,000 | 500 to 6000 | 1000 to 4000 |
| Wall thickness (microns) | 1.0 to 1,000 | 5.0 to 400 | 10 to 100 |
| Dispersed particles (microns) | 0.005 to 60 | 0.05 to 20 | 0.1 to 10 |
| Macro particles (microns) | 1.0 to 1,000 | 5.0 to 400 | 10 to 100 |
| Ratio of wall thickness to Outside microsphere diameter | 1:4 to 1:500 | 1:10 to 1:300 | 1:20 to 1:200 |

In certain catalyst applications of the invention, for example, when the microspheres contain in the single central cavity finely divided carbon particles, the hollow microspheres can have the dimensions shown below in Table II.

TABLE II

|  | Preferred | More Preferred |
|---|---|---|
| Diameter (microns) | 1200 to 6000 | 2000 to 4000 |
| Wall thickness (microns) | 10 to 200 | 20 to 100 |
| Dispersed particles (microns) | 0.05 to 10 | 0.1 to 5 |
| Macro particles (microns) | 10 to 200 | 20 to 100 |
| Ratio of wall thickness to outside microsphere diameter | 1:10 to 1:300 | 1:50 to 1:200 |

When use as substrates on which a catalyst solution is coated or impregnated the hollow microspheres can advantageously have diameters of 500 to 2000 microns and wall thickness of 50 to 800 microns and preferrably can have diameters of 600 to 1000 microns and wall thickness of 100 to 300 microns, respectively.

DISPERSED PARTICLES

The dispersed particles from which the hollow porous microspheres are made can be selected from a wide variety of materials and the dispersed particles and can be selected to have catalytic activity. The dispersed particles can include ceramic materials (including graphite and metal oxides), glasses, metals, metal glasses and plastics, and mixtures thereof.

The dispersed particles can be 0.005 to 60 microns in size, preferably, 0.05 to 20 and more preferably 0.1 to 10 microns in size. Generally a relatively narrow particle size distribution of particles are used. The smaller particles, e.g., 0.005 to 0.1 micron range size are referred to as colloidal size particles and particles in this size range are available in the form of sols or sol gels, or sol or sol gel precursor materials, and colloidal powders.

When colloidal size particles are used as the dispersed particles or as disperse particles having catalytic activity the particles can be purchased as sol dispersions or gels or as colloidal powders or can by conventional means be formed in situ, for example by chemical means from sol or sol gel precursor materials. A readily available source of colloidal size particles are the commercially available sol gel materials, colloidal powders, the ball clays and the bentonite clays. Further, there are now available, in concentrations of 10 to 50 weight percent solids, silica sols and metal oxide sols which can be used as dispersed particles, from the Nalco Company located in Oakbrook, Ill.

MACRO PARTICLES

Though strong hollow microspheres and hollow porous microspheres can be obtained from the dispersed particle compositions, it has been difficult to obtain uniform size openings or pore openings on the outer and inner microsphere wall surfaces. In accordance with a preferred embodiment of the invention macro pore openings of predetermined uniform and precise size can be obtained. This is done during the manufacture of the hollow porous microspheres by uniformly mixing with the dispersed particle composition uniform size macro particles which consist of combustible, vaporizable or meltable materials that will burn or decompose and vaporize or melt at temperatures above the blowing temperatures and below the temperatures at which the hollow microspheres are fired and sintered.

In order to obtain the desired size macro pores there is added to the dispersed particle composition and distributed throughout the composition a small proportion of combustible, vaporizable or meltable macro particles. The combustible, vaporizable or meltable particles are selected so that they are burned, vaporize or melt at temperatures below the melting temperatures of the dispersed solid particles, but at temperatures above the temperatures at which the microspheres are blown. The size of the combustible, vaporizable or meltable macro particles is selected such that they are about the same size or slightly larger in size than the wall thickness of the hollow microsphere being blown. In making microspheres with macro pores when the microspheres are heated and fired at elevated temperatures to sinter the dispersed particles, the macro pores are obtained which extend completely through the walls of the hollow microspheres.

The macro particles are selected to be of uniform size and generally spherically or spheroid in shape with preferably smooth wall surfaces. The particles are generally solid and made from combustible, decomposable, vaporizable or meltable materials. The meltable materials when heated will melt and spread to the adjacent particles. The macro particle material is selected such that it remains solid at the blowing and microsphere hardening temperatures and is removed at temperatures below the temperatures at which the firing and sintering step is carried out. Suitable materials for use as macro particles are carbon, naphthalene, anthracene, camphor, polyformaldehyde resins, and polyethylene, polypropylene and nylon beads or pellets. Various organic polymeric materials that meet the above criteria can also be used. In addition, relatively low melting temperature metals and glasses can be used as the macro particles.

The macro particle size is selected to be about the same or slightly larger in size than the thickness of the wall of the microsphere in which it is to create uniform size macro pores. Thus in microspheres having wall thickness of for example 10 to 200 microns, the macro particles would be about 14 to 280 microns in size, e.g., somewhat larger than the wall thickness. The diameter of the macro pore can of course be made larger than the thickness of the microsphere wall if such is desired.

The amount of the decomposable particles incorporated in the suspension or dispersion is not particularly critical insofar as the amount is sufficiently high so that all of the formed porous hollow microspheres contain at least one, preferably at least 5, and especially preferably at least about 10 to 20 decomposable particles in their walls. On the other hand, the amount of decomposable particles should not be so high that the blowing operation is impeded or that the mechanical strength of the microsphere wall is weakened.

The macro particles may be added to the dispersed particle composition in an amount of about 0.50 to 20%, preferably 1 to 10% and more preferably 2 to 6% of the dispersed particles plus macro particles volume. The desired amount of macro pores can be obtained without significant weakening of the microsphere wall.

The use of the macro particles allows the creation in the microsphere wall of macro pores of a predetermined size such that materials, such as solid or crystalline catalyst materials that are of a size of, for example, 5 to 100 microns, can be given a ready access path into the interior of the microsphere.

CERAMIC MATERIALS

The ceramic material used in the dispersed particle compositions from which the hollow porous microspheres are made are generally those that are presently known and used in the ceramic and catalyst industries. Ceramic materials, including metal oxides, that can be used as starting materials for making the microspheres are disclosed in Sowman U.S. Pat. No. 4,349,456. The selection of a particular ceramic material will depend on the desired properties of the microsphere including catalyst activity of the microspheres, the ease of processing and the availability and cost of the ceramic material or metal oxide material. For certain uses graphite particles can be used as the dispersed particle ceramic material. The conventionally used ceramic materials such as Alumina ($Al_2O_3$), Mullite ($3Al_2O_3.SiO_2$), Cordierite ($2MgO.2Al_2O_3.5SiO_2$), Zircon ($ZrO_2.SiO_2$), and Zirconia ($ZrO_2$) can be used. Naturally occurring clay materials such as Kaolinite, montmorillonite, illite and bentonite can be used. The ball clay materials can also be used. A preferred ceramic material for use as dispersed particles is alumina ($Al_2O_3$) sold by Alcoa under the trade names of Alcoa "A-16" and "A-17".

GLASS MATERIALS

The constituents of the glass material from which the dispersed particle compositions can be made are widely varied to obtain the desired physical characteristics of the hollow glass microspheres. The constituents of the glass particles, depending on their intended use, can be synthetically produced glasses or naturally occurring glasses. The constituents of the glass can be selected and blended to have sufficient strength when hardened and solidified to support a substantial amount of weight. Naturally occurring glass materials such as basaltic mineral compositions can also be used. The use of these naturally occurring glass materials can in some cases substantially reduce the cost of the raw materials used. The glass materials disclosed in applicant's U.S. Pat. No. 4,303,431 can be used as starting materials for the hollow microspheres. The glass materials disclosed in the De Vos U.S. Pat. No. 4,059,423 can also be used.

METAL MATERIALS

The hollow microspheres can also be formed from dispersed metal particles such as iron, steel, nickel, silver, gold, copper, zinc, tin, tungsten, lead, aluminum, magnesium, cobalt, platinum and palladium and the like, and mixtures thereof. The metals disclosed in the Schmitt U.S. Pat. No. 3,264,073 and in Farnand U.S. Pat. No. 3,674,461 can also be used as starting materials for the hollow microspheres.

METAL GLASS MATERIALS

There are a wide variety of metal glass alloy compositions which can be used as starting materials to make hollow porous metal glass microspheres. The term metal glass(es) as used herein is intended to mean the metal alloy materials and compositions which on rapid cooling from a temperature above their liquidus temperature to a temperature below their glass temperature can form amorphous solids. The metal glass alloys compositions have been broadly described as (1) metal-metalloid alloys, (2) transition metal alloys and (3) simple metal alloys. The known metal glass alloy compositions include precious metal alloys, alkaline earth metal alloys, rare earth metal alloys and actinide metal alloys. The dispersed metal glass particles can be made from the metal glass alloy materials disclosed in the applicant's U.S. Pat. No. 4,415,512.

PLASTIC MATERIALS

The plastic materials that can be used as starting materials to make hollow porous microspheres are those disclosed in applicant's U.S. Pat. No. 4,303,603. Other plastic materials that can be used as starting materials are nylon, latex particles and aqueous dispersions of TEFLON (PTFE).

DESCRIPTION OF THE INVENTION

1. The microsphere catalyst can be prepared by coating or impregnating the hollow porous microspheres with the catalyst dissolved in an organic or inorganic solvent solution. The coating or impregnating step can be carried out by spraying the microspheres or immersing the microspheres in the coating or impregnating solution. The coating or impregnating solution displaces the air or gas within the hollow interior of the microspheres, fills the hollow interior of the microsphere and the pores or interconnecting voids in the microsphere walls with the catalyst solution. The coated or impregnated microspheres are separated from the solution, heated and dried to deposit the catalyst. This procedure can be repeated, if desired, to build up the catalyst content in the central cavity of the microsphere. The microspheres with the deposited catalyst can then be treated in a conventional manner to activate the catalyst by subjecting them to a reducing atmosphere or an oxydizing atmosphere at elevated temperature, or other treatment.

2. The microsphere catalyst can also be prepared by filling the catalyst with a support and then coating or impregnating the hollow porous microspheres and support with the catalyst. The hollow porous microspheres can be filled with a catalyst support by immersing the microspheres in a solution, slurry or sol dispersion of the support and, e.g. applying pressure to the solution, slurry or sol dispersion. The microspheres can also be filled by placing the hollow porous microspheres on a porous belt, applying a suction under the belt and then spraying or immersing the microspheres in the slurry or sol dispersion. In each case the solution, slurry or sol dispersion displaces the air or gas within the hollow interior of the microsphere, fills the hollow interior of the microsphere and the pores or interconnecting voids in the microspheres walls with the solution, slurry or sol dispersion of the catalyst support. The microspheres can be, if desired, partially or entirely filled, or the pores or interconnecting voids in the microsphere walls can be filled with the catalyst support.

The microspheres, after the filling step, are processed (i.e. dried, heated, washed, etc., as the case may be) as required to deposit the catalyst support. The microsphere can then be heated to obtain the desired physical characteristics of the catalyst support. The catalyst support in finely particulate form is deposited on the inner wall surface of the microsphere and/or fills the hollow interior of the microspheres and the pores or interconnecting voids of the microspheres. The drying step removes the liquid phase of the slurry or sol from the microsphere and the catalyst support forms small particles of catalyst support which particles within the microsphere tend to agglomerate, a small degree, during the drying step, thereby preventing them from leaving the central cavity. The small particles in the pores or interconnecting voids of the walls of the microsphere adhere to the sides of the interconnecting voids. The adherence of the catalyst support to the sides of the interconnecting voids has the effect of reducing the pore size, i.e. the cross-sectional area of the interconnecting voids and at the same time through the presence of the catalyst support substantially increasing the surface area of the interconnecting voids in the microsphere walls. The filling of the hollow interior of the microsphere with catalyst support also substantially increases the available surface area of the hollow porous microspheres for deposit of catalyst.

The thus treated microspheres are further treated by coating or impregnating the hollow microspheres that now contain a catalyst support with catalyst. The catalyst can be applied by immersing the microspheres in a solution, slurry or sol dispersion of the catalyst in the manner discussed above and filling the interior of the microsphere and the interconnecting voids of the walls of the microspheres in a manner such that the catalyst support contained in the interior of the microsphere and in the interconnecting voids of the microsphere walls are completed coated, or substantially completely coated with the catalyst. The hollow microspheres are separated from the catalyst solution, slurry or sol dispersion and dried and if desired washed to remove any excess of the catalyst. The hollow microspheres containing the catalyst on the catalyst support can then be treated, as necessary, to activate the catalyst, e.g. by calcining, and/or subjecting the catalyst to any oxydizing or reducing atmosphere.

3. The catalyst can be prepared by filling the microspheres with catalyst or catalyst and catalyst support. The hollow porous microspheres can be filled with a catalyst or catalyst and catalyst support by immersing the microspheres in a melt, slurry or sol dispersion of the catalyst or catalyst and support, by placing the microspheres on a porous belt, applying a suction under the belt and then spraying or immersing the microspheres in catalyst or catalyst and catalyst support melt, slurry or sol dispersion. The melt, slurry or sol dispersion displaces the air or gas within the hollow interior of the microsphere, fills the hollow interior of the microsphere and the pores or interconnecting voids in the microsphere walls with the melt, slurry or sol dispersion of the catalyst or catalyst and support. The microspheres can be, using the above described methods, partially or entirely filled, or only the pores or interconnecting voids in the microsphere walls can be filled. The microspheres after the filling step are heated and dried to deposit the catalyst or catalyst and support, and if desired washed. The dried microspheres can then be treated in a conventional manner, e.g. heated to calcine the catalyst or catalyst and support to obtain the desired physical and catalytic characteristics and properties of the catalyst or catalyst and support.

The drying step removes the liquid phase of the slurry or sol dispersion and deposits the catalyst or catalyst and support within the hollow interior of the microsphere and on the inner wall surface of the mirosphere and on the wall surfaces of the interconnecting voids.

The catalyst or catalyst and catalyst support form small particles of catalyst or catalyst and support. The catalyst or catalyst and support particles within the microsphere tend to agglomerate, a small degree, during the drying and/or calcining step, thereby preventing them from leaving the central cavity of the microspheres. The small particles of catalyst or catalyst and support in the pores or interconnecting voids of the walls of the microspheres adhere to the walls of the interconnecting voids. The adherence of the catalyst support and catalyst to the walls of the interconnecting voids has the effect of reducing the pore size, i.e. the cross-sectional area of the interconnecting voids and at the same time through the presence of the catalyst or catalyst and catalyst support substantially increasing the surface area of the pores in the microsphere walls. The filling of the hollow interior of the microsphere with catalyst or catalyst and support also substantially increases the surface area of the catalyst available to the reactant. The hollow microspheres containing the catalyst or catalyst and support can then be treated as necessary to activate the catalyst or catalyst and support, e.g. by subjecting the microsphere to a calcining step and/or a reducing or an oxydizing atmosphere.

4. The microsphere catalyst can be prepared by coating a support with the desired catalyst and filling the hollow porous microsphere with the catalyst coated on the support. The catalyst on the support can be milled or ground to an appropriate size and in the form of a slurry or sol dispersion used to fill the hollow microspheres. The microspheres can be filled with the catalyst on the support by immersing the microspheres in a slurry or sol dispersion of the catalyst on the support, or by placing the microspheres on a porous belt, applying a suction under the belt and then spraying or immersing the microspheres in the slurry or sol dispersion of catalyst on support.

The slurry or sol dispersion catalyst fills the hollow interior of the microsphere and the pores or interconnecting voids in the microsphere walls with catalyst. The microspheres can by using the above described methods, partially or entirely filled, and/or the pores or interconnecting voids in the walls can be filled with catalyst.

The microspheres after the drying step are, if desired, washed. The dried microspheres can then be further treated to activate the catalyst or to otherwise obtain the desired physical and catalytic characteristics and properties of the catalyst on the support. The drying step, where a slurry or sol dispersion is used, removes the liquid phase from the slurry or sol and forms small particles of the catalyst on support within the hollow interior of the microsphere. The drying step as mentioned above tends to a small degree to agglomerate the catalyst particles, thereby preventing them from leaving the central cavity of the microspheres.

The small particles of catalyst on support in the pores or interconnecting voids on the walls of the microspheres adhere to the sides of the interconnecting voids. The heating steps enhance and strengthen the adhesion.

The adherence of the catalyst on the support to the sides of the interconnecting voids has the effect of reducing the pore size, i.e. the cross-sectional area of the interconnecting voids and at the same time through the presence of the catalyst on the support increasing the surface area of the pores in the microsphere walls. The filling of the hollow interior of the microspheres with the catalyst on the support also substantially increases the surface area of the catalyst available to the reactant. The microspheres containing the catalyst on the support can be treated as necessary to activate the catalyst, e.g. by subjecting the catalyst to a calcining step or to anoxydizing or a reducing atmosphere.

5. The microspheres containing a catalyst can be coated with an inorganic selective membrane or for low temperature operations an organic selective semiphermeable membrane.

The microspheres containing a catalyst can be treated to coat at least the outer pore surface or area of the wall of the microsphere with an inorganic selective membrane. The inorganic selective membrane is applied by coating the microspheres with a sol dispersion of the desired coating material. The particular sol dispersion material, particle size and concentration of the particles in the sol dispersion and the subsequent heating temperature and time determine the micro pore size of the resulting inorganic selective membrane. The micro pore size can be selected to exclude specified materials, e.g. catalyst poisons and/or to selectively admit for contact with the catalyst, contained on and/or in the hollow microspheres, specific chemical constituents of a reactant gas or liquid feed to the reaction. The use of an inorganic selective membrane allows use of the catalyst at relatively high temperatures.

The microspheres containing a catalyst can be treated to coat at least the outer pore surface or area of the wall of the microsphere with an organic selective semipermeable membrane. The oganic selective membranes have the advantage of a higher degree of selectivity being obtainable but the restriction that they can only be used at relatively low process reaction temperatures of, for example, about 300° to 400° C. The organic selective semipermeable membrane can be applied in the manner discussed in applicant's copending application Ser. No. 657,090 filed Oct. 3, 1984 which is briefly discussed below.

The inorganic selective membranes and the organic selective semipermeable membranes prevent the catalyst encapsulated in the microsphere from leaving the microsphere through the pores entrance means. Only specific liquids, gases and/or organic (or inorganic) molecules of predetermined molecular size which is smaller in size than the pore size of the selective membrane can enter or leave the single central cavity of the microsphere through the selective membrane.

6. The microsphere catalyst can be used to carry out catalytic reactions including petroleum hydrocarbon processes and chemical processes and to carry out emission control processes.

In carrying out the present invention the catalyst or catalyst support can be applied to the hollow porous microspheres in the form of chemical precursors of the desired catalyst or catalyst support. The chemical precursors can undergo on the surface and/or in the central cavity of the hollow microspheres a chemical reaction, including a decomposition reaction to form the desired catalyst or catalyst support. The catalyst or catalyst support can also be applied to the hollow microspheres in the form of a melt of the catalyst or catalyst support. An example of a melt of a catalyst or catalyst support would be a high boiling hydrocarbon, which is subsequently heated and decomposed to form a finely divided active carbon. The finely divided active carbon can function either as a catalyst or catalyst support. Suitable precursors for the carbon particles are pitch and Saran. An Example of a chemical precursor material which is decomposed to form a catalyst is an aqueous solution of chloroplatonic acid which on drying the solution and decomposing the chloroplatonic acid forms a deposit of platinum.

DESCRIPTION OF CATALYST

The hollow porous microspheres can be used as catalyst substrate and catalyst containers for a wide variety of catalyst. For practical purposes, it is convenient to breakdown the use of catalyst reactions into three major categories: petroleum refining, chemical processes and emission control.

A brief description of the major categories of catalyst reactions and catalysts used in each is provided below.

Petroleum Refining

Catalytic cracking—In the refining of petroleum hydrocarbons the catalytic cracking of hydrocarbons is carried out primarily to increase the yield of gasoline fractions. The principal catalyst used are alumina-silica and more recently natural and synthetically produced alumino-silicate zeolite molecular sieves. The catalytic cracking reaction can be carried out in a moving bed catalytic cracking apparatus.

Alkylation—In order to increase the yield of gasoline components $C_3$ and $C_4$ normal and isohydrocarbons are reacted in contact with concentrated sulfuric acid or hydrofluoric acid to produce $C_7$ and $C_8$ isohydrocarbons.

Hydrotreating—Hydrocarbon streams containing sulfur and/or nitrogen are treated with a catalyst in the presence of hydrogen. The hydrotreating is carried out to remove sulfur and/or nitrogen from a wide variety of petroleum fractions including naptha, kerosene, gas oil and residual oil fractions. Hydrotreating catalyst include alumina impregnated with molybdenum or tungsten oxide or molybdenum or tungsten sulfide as the active component and cobalt oxide or sulfide or nickel oxide or sulfide as activity promoters.

Hydrocracking—Petroleum fractions are contacted with a hydrotreating catalyst in the presence of hydrogen to crack the feed to upgrade the products for use as gasoline, heating oil and kerosene, and to upgrade feed stocks for use in other processes. Hydrocracking catalyst include noble metals such as platinum and/or palladium on an alumina or molecular sieve zeolite support, and cobalt or nickel with tungsten or molybdenum on an alumina or molecular sieve zeolite support.

Catalytic Reforming—Low octane components of petroleum fractions are treated to form higher octane components, particularly for use as blending components in no-lead or low-lead gasolines. The reforming catalyst used includes platinum on alumina support and platinum and rhenium on alumina support. Hydrogen gas is a principal by-product and is recovered for use in other refinery processes.

Chemical Processes

Polymerization—Polymerization processes are carried out to make high density polyethylene, polypropylene, linear low density polyethylene, polyvinyl chloride, polystyrene and urethane. The Ziegler-Natta catalyst which are a combination of titanium or vanadium halide and alumina or magnesium alkyl are used in the polymerization of polypropylene and high density polyethylene. Organic peroxides are used to initiate the polymerization of various monomers to make low-density polyethylene, polyvinyl chloride and polystyrene. Polyurethanes are manufactured by using organo-metals, e.g. organic tin compounds, and a tertiary amine catalyst.

Oxidation Reactions—The production of nitric acid is carried out with a noble metal, e.g. platinum or palladium on a support. The production of vinyl chloride is carried out with copper chloride on an alumina support to carry out the oxychlorination step.

Hydrogenation—Olefin hydrocarbons, aromatic hydrocarbons and nitro hydrocarbons, edible and inedible oils, margarine, shortening and fatty amines are treated in the presence of a nickel catalyst and hydrogen to form the corresponding compounds with an increased hydrogen content.

Dehydrogenation—Styrene is produced from ethyl benzene in the presence of a promoted iron catalyst. Hydrogen is a by-product of the reaction.

Emission Control

Automotive Exhaust—Automotive, truck and other internal combustion engine exhausts are treated to remove carbon monoxide, hydrocarbons and nitrous oxides ($NO_x$) from the exhaust. The catalyst uses noble metals such as platinum, palladium, rhenium and rhodium and mixtures thereof on ceramic supports, such as alumina.

Industrial Waste Gases—Noble metals on supports as mentioned immediately above are used to control emissions from incinerators, ovens, wood stoves and nitric acid plants.

Electric Power Generating Plant Stack Gases—activated carbon, carbon molecular sieve and copper oxide catalysts are used to remove sulfur dioxide and nitrous oxides ($NO_x$) from stack gases.

The catalyst can be applied to the hollow porous microspheres in the form of solutions, sol dispersions and slurries of the catalyst. The catalyst can also be applied to the hollow porous microspheres in the form of chemical precursors of the desired catalyst. The chemical precursors after application to the hollow microspheres can be treated to undergo a chemical reaction, including a decomposition reaction to form the desired catalyst.

The normally liquid catalyst, e.g. concentrated sulfuric acid used in alkylation reactions, can be treated to immobilize the catalyst, e.g. the catalyst can be treated with an inert colloid to gel the catalyst and the gel catalyst can be applied to coat or fill the hollow microspheres. Alternatively, the microspheres can be coated or filled with the liquid catalyst and then treated with an inert colloid to gel the liquid catalyst. Examples of inert colloids that can be used are silica, alumina and graphite.

The resin catalysts can also be used by coating or filling the hollow microspheres with the resin catalyst. Suitable resin catalysts are those produced by the Rohm and Haas Company under the trade name Amberlyst. The Amberlyst catalyst resins are marketed in the form of small insoluble beads. Amberlyst 15, for example, is a sulfonic acid resin which can be used to catalyze esterification, hydration and oligerization reactions.

CATALYST SUPPORTS

In order to increase the activity of the catalyst, catalyst support materials can be added to the hollow porous microspheres. The catalyst supports are those conventionally used in the art with the catalyst. Suitable catalyst supports include alumina, silica, silica-alumina, alumina silicate molecular sieve zeolites, finely divided carbon and carbon molecular sieves. A readily available source of colloidal size catalyst support materials are the commercially available sol gel materials, colloidal powders, the ball clays and the bentonite clays. Further, there are now available in concentrations of 10 to 50 percent solids, silica sols and metal oxide sols which are suitable for use as catalyst supports.

The catalyst supports can be added to the microspheres in the form of a solution, sol dispersion or slurry of the support in a solvent, i.e. continuous phase. The catalyst supports can also be added to the microspheres in the form of a melt. The solution, sol dispersion or slurry can be applied to the microspheres by coating or impregnating the microsphere with the solution, sol dispersion or slurry. The microspheres can be treated with the support to completely fill the microspheres, partially fill the microspheres, fill the pores and interconnecting voids of the microspheres or to coat the outer wall surface of the microspheres.

Where the entire microsphere is filled with, e.g. a high concentration of a sol dispersion of alumina or silica particles in an aqueous continuous phase, the alumina or silica particles can be selected to be less than one half the size of the microsphere pores, or where macro pores are present less than one half the size of the macro pores.

The microspheres can be completely filled with the sol dispersion and then dried to remove the aqueous continuous phase. After drying the microspheres containing the sol dispersion the microspheres can be heated to a temperature of 600° to 800° C. to remove the remainder of any aqueous phase, and to sinter the dispersed particles to form within the single central cavity of the microsphere a lattice work of the sintered alumina or silica particles. The heating to 600° to 800° C. can also activate the supports.

The lattice work continues from the central cavity, through the interconnecting channels to the pores in the outer surfaces of the microsphere's walls. In some applications, the lattice work of alumina or silica particles are broken up by agitation of the microspheres to form in the central cavity loose agglomerates of the alumina or silica particles.

In another embodiment of the invention the microspheres may be filled with only a sufficient amount of the sol dispersions such that the alumina or silica particles only deposit on the inner wall surface, in the interconnecting voids and on the outer wall surfaces of the microsphere's walls.

In still another embodiment of the invention the size of the catalyst support particles in the sol dispersion or slurry are selected to be big enough such that they do not pass through the interconnecting channels, but instead deposit on the outer wall surfaces and in the entrances on the outer wall surfaces of the microsphere walls.

The catalyst supports can be applied to the hollow porous microspheres in the form of chemical precursors of the desired catalyst supports. The chemical precursors after application to the hollow microspheres can be treated to undergo a chemical reaction, including a decomposition reaction to form the desired catalyst supports.

The catalyst support can be activated before or after adding the catalyst to the hollow porous microsphere. The catalyst can be added to microspheres and catalyst supports in the form of a solution, sol dispersion or slurry of the catalyst. The catalysts can also be added in the form of a melt.

FILLING THE MICROSPHERE

The method used to fill the hollow porous microspheres with the catalyst is dependent upon the particular system and must be conducted so that the activity of the catalyst is not adversely affected in the process. Prior to filling the microspheres with catalyst it may be necessary or desirable to treat the microspheres to remove any residual amounts of binder material that may have been present during the microsphere manufacturing procedure.

In some cases it is sufficient to merely suspend the microspheres in a liquid carrier medium in which the catalyst is dissolved, suspended or dispersed, and to allow the catalyst to flow, or to diffuse by capillary action, through the entrance means or both the entrance means and pores in the walls of the porous hollow microspheres, depending on the size of the catalyst, into the hollow interior of the microspheres. The suspension can be gently stirred by mechanical mixing, to ensure homogeneity of the system and uniformity of the amount of catalyst in contact with individual microspheres. It is also preferred that the liquid carrier be capable of wetting the material forming the walls of the microspheres to assist in the filling process. Wetting agents which are inert to the catalysts can be added to the liquid carrier mediun for this purpose.

The concentration of the catalyst in the liquid carrier and the amount of catalyst relative to the total volume or number of the microspheres will be selected depending on the nature and type of catalyst and the catalytic process and on the internal volume of the microspheres and can be readily determined by the skilled practitioner.

While the driving force of capillary action can be sufficient to fill the hollow microspheres with the suspended, dispersed or dissolved catalyst, this technique often requires long times, on the order of about several hours, to fill all of the microspheres, and may not be practical where the solid particles forming the microsphere walls and defining the interconnecting voids or channels and the entrance means are not sufficiently wetted by the liquid phase of the catalyst solution, suspension or dispersion.

Therefore, according to an embodiment of the invention, the driving force for filling the hollow microspheres with the catalyst and liquid medium is increased by applying pressure to the system. The applied pressure can be fluid pressure, e.g. hydrostatic pressure, isostatic pressure, pneumatic pressure or dynamic pressure, e.g. centrifugal force.

Generally, the amount of the applied pressure will not be particularly critical insofar as the pressure is not so great as to rupture the walls of the microspheres and which will maintain flow of the catalyst-liquid medium system into the microspheres. Pressures in the range of from about 3 psi to about 30 psi, preferably from about 5 psi to about 25 psi have been found to be satisfactory. Preferably, the pressure is increased gradually. The pressure should be maintained until at least substantially all of the microspheres are filled with the catalyst and liquid medium. Generally, the time required to fill the microspheres will be inversely proportional to the applied pressure and to the size and number of entrance means and pores in the walls of the microspheres which connect the exterior of the microspheres to the hollow interior of the microspheres. Times on the order of from about 30 seconds to about 60 minutes, generally from about 1 minute to about 40 minutes are satisfactory.

One preferred filling method is to simply load a pressure vessel with the microspheres and thereafter to fill the closed pressure vessel with the catalyst-containing liquid medium under positive pressure using a suitable pressure pump.

Another method for filling the microspheres is to displace the gas normally contained in the microspheres with a gas that readily dissolves in the carrier liquid or catalyst solution, e.g. carbon dioxide or propane.

In a preferred embodiment of the invention a relatively simple technique for filling the hollow microspheres is to "pull" the catalyst-liquid medium system into the microspheres through the entrance means and/or pores. That may be done by forming a thin layer, preferably a single or several layers, of the microspheres on a microporous sheet or belt and applying a vacuum to the reverse side of the sheet or belt whereby the catalyst-liquid medium system will be sucked into the hollow interior spaces of the microspheres. If desired, a positive pressure can simultaneously be applied to the catalyst-liquid medium system. The belt may be a moving belt such that the filling procedure may be made to be continuous.

In filling the central cavity of the microspheres using an applied vacuum with, for example, colloidal size particles, it is found that the non interruption of the flow of the particles, the direction of flow of the particles and the application of the vacuum are important. The continuous flow in the same direction of the colloidal size particles allows the particles to enter the microsphere from one side and allows the particles build up to occur inside of the central cavity on the opposite side of the microspheres until the central cavity is filled with the colloidal size particles.

In filling the microspheres, it is generally sufficient to use an excess liquid medium and to carry out the filling operation for a period of about 20 to 60 minutes, preferably 30 to 40 minutes to assure adequate filling of the microspheres with the dissolved or suspended catalyst and liquid medium.

Depending on the microsphere catalyst that it is desired to obtain, the microsphere may be substantially completely fill with catalyst, only the interconnecting voids may be filled and the outer surface coated, or only the outer surface may be coated with catalyst. Where the microsphere is filled with catalyst, depending on the concentration of catalyst in the catalyst solution, slurry or sol dispersion, the microspheres may contain solid particulate catalyst in the single central cavity and/or the interior wall surfaces may have deposited thereon the catalyst.

Where a catalyst support is used, as discussed above, the catalyst is deposited on the support. Generally the procedures for filling the microspheres with catalyst are also applicable to filling the microspheres with catalyst supports. The procedure used can be repeated as desired to build up the catalyst or catalyst support contained in the central cavity of the microspheres.

CATALYST IMMOBILIZATION

After the microspheres are filled with catalyst it may be desirable or necessary to treat the microspheres and catalyst to immobilize the catalyst such that the catalyst is not readily removed from the hollow interior of the microspheres.

The treatment required in each instance will depend on the particular catalysts and whether the microspheres have microsphere pores or microsphere pores and macro pores.

In some situations it may be sufficient to merely agitate the microspheres to cause sufficient agglomeration, e.g. loss of suspending particle charge leading to the development of cohesive forces, or an increase in catalyst crystal or particle size, such that the catalyst is not easily removed from the interior of the microspheres. In other cases agitation or agitation coupled with heating to a slightly elevated temperature is sufficient to obtain the desired agglomeration and increase in catalyst particle size.

In another embodiment a small amount of an organic or inorganic binder material is added to the catalyst sol dispersion or slurry, which on drying the microspheres and catalyst provides sufficient adhesion of the catalyst particles to each other that the catalyst particles are retained within the microspheres until the catalyst can be made to aggolomerate or until the microspheres and catalyst can be treated to close the microsphere entrance means with an immobilizing membrane. The organic binder is substantially removed during a subsequent heating step to agglomerate the catalyst or to activate the catalyst. The inorganic binder material can be removed or if inert to the catalyst reaction can be allowed to be retained with the catalyst.

In an embodiment of the invention after the microspheres are filled with catalyst, e.g. small solid particles, the hollow microspheres are treated with a suitable solution, sol dispersion or slurry containing an inorganic dissolved or dispersed material suitable for forming an inorganic immobilizing membrane. The microspheres are then dried to remove the continuous phase and deposit on the outer wall surfaces and in the interconnecting voids of the microsphere walls small solid particles. For example, where a silica sol dispersion is used to form the immobilizing membrane, after treatment with the silica sol dispersion, the microspheres are heated to a temperature of about 400° to 800° C. to fire and sinter the silica particles. The silica particles link-up to form a porous lattice work of particles across the interconnecting voids, sinter to the surface of the particles forming the interconnecting voids and the firing removes the liquid phase from the dispersed silica particles.

The forming of a porous lattice work of sintered colloidal size silica particles in the interconnecting voids substantially decreases the size of the interconnecting voids and/or where macro pores are present in the microsphere wall also substantially reduces the size of the macro pores such that the catalyst contained in the hollow central cavity of the microsphere is immobilized.

Various materials can be selected to form the immobilizing membrane, e.g. alumina, silica, metals, metal salts and ceramics. The material selected is such that it will not adversely effect the catalytic activity of the catalyst and such that it can withstand the conditions of temperature and chemical environment to which the catalyst is subjected.

Accordingly, it is sufficient to use any inorganic immobilizing means which will effectively retain the catalyst in the hollow interior of the microspheres while permitting influx and outflow of liquids, gases, reactants, products and by-products, etc., which are required for the process and/or for the non-contamination of the catalyst.

INORGANIC SELECTIVE MEMBRANES

In another embodiment of the invention the material used to form the immobilizing membrane can be chosen to deposit an inorganic selective membrane having a predetermined micro pore size. The pore size of the selective membrane can be chosen such that only selected constituents of a process stream or chemical mixture are allowed to pass through the membrane and to come into contact with the catalyst and to react, while the remainder of the process stream or chemical mixture is prevented from contacting the catalyst. The use of a selective inorganic membrane can thus be used to combine in a single process a selection and separation with a catalyst reaction. The use of the selective membrane can also lengthen the catalyst activity and catalyst life by excluding from contact with the catalyst materials that may tend to deactivate or poison the catalyst.

Materials that are suitable for forming inorganic selective membranes are boehmite (gamma-AlOOH), alumina and silica.

ORGANIC SELECTIVE SEMIPERMEABLE MEMBRANES

In another embodiment of the invention where the catalyst reaction is carried out at relatively low temperatures organic membranes may be used as immobilizing and/or selective membranes. In accordance with this embodiment, after the microspheres are filled with catalysts, e.g. small solid particles, the hollow microspheres are treated with a suitable solution, sol dispersion or slurry containing an organic dissolved or dispersed material suitable for forming an organic immobilizing membrane. The microspheres are then dried to remove the continuous phase and deposit on the outer wall surfaces and in the interconnecting voids of the microsphere walls a thin organic membrane. The organic membrane can be selected to be permeable to the reactants and reactant products while at the same time immobilizing the catalyst. The organic membrane may also be used to improve the catalyst selectivity by admitting only certain reactants.

The forming of the permeable organic membrane, seals off the interconnecting voids and the macro pores in the microspheres wall such that the catalyst contained in the hollow central cavity of the microsphere is immobilized.

Various organic materials can be selected to form the immobilizing membrane, e.g. organic polymeric materials such as silicones, acrylics, and nylons. The materials are selected such that they will not adversely effect the catalytic activity of the catalyst and such that they can withstand the conditions of temperature and chemical environment to which the catalysts are subjected.

Accordingly, it is sufficient to use an organic immobilizing means which will effectively retain the catalyst in the hollow interior, will permit influx and outflow of liquids, gases, reactants, products and by-products, etc. which are required for the process and will exclude from the catalyst other materals, e.g. those materials that would contaminate the catalyst.

In an embodiment of the invention the material used to form the immobilizing organic membrane can be chosen to deposit an organic selective membrane having a predetermined permeability for molecular size materials.

The permeability of the organic selective membrane can be chosen such that only selected constituents of a process stream or chemical mixture are allowed to pass through the membrane and to come into contact with the catalyst and to react, while the remainder of the process stream or chemical mixture is prevented from contacting the catalyst. The use of an organic selective semipermeable membrane can thus be used to combine in a single process a selection and separation with a catalyst reaction. The use of the selective membrane can also lengthen the catalyst activity and catalyst life by excluding from contact with the catalysts materials that may tend to deactivate or poison the catalysts.

Any suitable method can be used for depositing the organic semipermeable membranes. For instance, the microspheres can be immersed in a dilute solution of a film-forming polymer or a polymer forming system, preferably while applying mild agitation to the mixture to ensure homogeneity and uniform formation of the film on all of the microspheres. It is also preferred to carry out the contact with a small overpressure on the system to force the polymer film into the microspheres pores and macro pores, as well as between and among the individual sintered particles of the microsphere walls defining the microsphere's interconnecting channels, this serving to strengthen the bond between the formed membranes and the microspheres. It should be noted that the application of pressure to the film forming solution in which the microspheres are immersed can be analogized to the application of a vacuum to the bore of hollow porous filaments to which a permselective polymer coating is applied from the exterior, such as taught in U.S. Pat. Nos. 4,230,463, and 4,214,020. The coating process is generally suitable for applying a depositable film forming material to form a deposit of a semipermeable membrane in the microsphere pores and macro pores of individual microspheres over essentially the entire surface areas of the hollow microspheres. The deposited films are sufficiently thin to provide high flux rates of reactant gas or liquid constituents having a molecular size below the "cut-off" size or "cut-off" molecular weight of the deposited semipermeable film. The "cut-off" size or weight refers to the maximum molecular size or weight of reactant constituents which can diffuse through the semipermeable membrane.

In further detail, the depositable material, i.e., a material suitable for forming the coating, desirably has a sufficiently large molecular size (if dissolved in the solvent) or a sufficiently large particle size (if suspended in the solvent, e.g. as a colloidal dispersion) that the depositable material does not readily pass through the pores in the walls of the hollow microspheres when subjected to pressure. Thus, with microspheres having pores of generally larger diameters, depositable materials which have larger sizes when in the coating liquid are frequently desired. In some instance, it is desirable to employ depositable materials which, when in the liquid vehicle, have sufficiently small sizes that they can enter, instead of bridge, pores in the microspheres. The depositable material may directly form the coating when deposited, or the deposit of the depositable material may be further treated, e.g. by cross-linking, to form the desired coating.

The coating liquid generally comprises a solvent (or vehicle) for the depositable material. The solvent should be capable of dissolving the depositable material or be capable of suspending a finely-divided depositable material, e.g. having particle diameters less than about 1 micron, e.g. about 5000 angstroms (i.e., colloidal size). Desirably, the coating liquid contains substantial amounts of solvent, e.g. a major amount of solvent, such that during deposition of the depositable material on the hollow microspheres, depositable material, which is not forcibly retained in the microsphere pores and macropores due to adhesion to the solid wall material and/or due to the presence of the applied pressure, can be redissolved or otherwise removed from the hollow microspheres. Also, the coating liquid contains sufficient amounts of solvent such that the coating liquid exhibits a viscosity at temperatures employed in the coating which viscosity is advantageously low to enable relatively rapid, adequate permeation of the coating liquid through a dense mass of the microspheres.

The contact of the coating liquid containing the depositable material with the mass of microspheres in order to effect the desired deposition is advantageously provided by immersion of the microspheres in the coating liquid. The immersion of the hollow microspheres in the coating liquid may be effected in any suitable manner. For instance, the mass of microspheres may be poured into the coating liquid. However, it is generally preferred that the coating liquid be added to a retaining vessel containing the mass of microspheres.

The coating liquid may be unagitated or may preferably be agitated, e.g. by circulating the coating liquid through the retaining vessel to assist in maintaining the suspension of the depositable material (if the depositable material is in particulate form in the coating liquid) and in providing desirable distribution of the coating liquid through the microsphere mass.

The hollow microspheres can be subjected to the applied pressure from the exterior to the interior at least while immersed in the coating liquid. The pressure drop is desirably maintained for a time (either intermittent or preferably continuous) sufficient to provide the desired deposit.

After the removal of the coated microspheres from the coating liquid, the microspheres may be immersed in at least one additional coating liquid, which additional coating liquid may or may not be essentially the same as that of the first coating liquid, in order to provide two or more coatings on the hollow microspheres or to chemically affect at least one preceding deposit, e.g. by cross-linking or the like. Cross-linking or other procedures which chemically affect the deposit may be provided by contact with a suitable liquid or gaseous agent. The deposits on the hollow microspheres may or may not be dried (i.e. the remaining solvent removed) or otherwise treated intermediate the immersions.

The resulting coating (or coatings) are relatively uniform throughout all the pores and interconnecting voids and macropores. Generally, the coating has an average thickness of up to about the microsphere wall thickness, preferably about ½ to 1/50 of the microsphere wall thickness. Frequently, the average thickness of the coating is less than about 5, and may even be about 1 micron or less. Advantageously, the coating is substantially permanent in the pores and interconnecting voids and macropores and thus does not unduly separate from the hollow microsphere during storage or use of the microspheres in carrying out catalytic reactions.

The hollow microspheres prior to being coated are porous, i.e. have continuous channels for fluid flow extending between the exterior and interior surfaces. Frequently, the microsphere pores have an average cross-sectional diameter of from about 1000 to about 50,000 angstroms (0.1 to 5 microns) and in some hollow microspheres, the cross-sectional diameter of the pores or interconnecting voids can be about one to about 5 microns.

Passage across the semipermeable membrane may be by chemical or molecular diffusion and/or by solvation and evaporation and is dependent on the molecular spacing of the coating material and the material permeating through the membrane.

CONTINUOUS LIQUID PHASE

The liquid phase for the solutions, slurries or sol dispersions described herein can be aqueous or non-aqueous. The liquid phase can act as a solvent for one or more of the ingredients, for example, the catalysts, the catalyst supports, the binders for the catalyst supports or catalysts, the immobilizing membrane precursors or the selective membrane precursors.

The aqueous liquid phase can comprise water and/or water and water soluble solvents. The binders that can be used for catalyst or catalyst supports in aqueous continuous liquid phase compositions include acrylic polymers, acrylic polymer emulsions, ethylene oxide polymer, hydroxethyl cellulose. methyl cellolose, polyvinyl alcohol and xanthan gum.

The non-aqueous liquid phase can comprise organic solvents such as acetone, ethyl alcohol, benzene, bromochloromethane, butanol, diacetone, ethanol, isopropanol, methyl isobutyl ketone, toluene, trichloroethylene and xylene.

The binder materials that can be used for catalyst or catalyst supports in non-aqueous liquid phase compositions include cellulose acetate, butyrate resin, nitro cellulose, petroleum resins, polyethylene, polyacrylate esters, polymethyl methacrylate, polyvinyl alcohol, polyvinyl butyral resins, and polyvinyl chloride.

The binder materials are used in a relatively small amounts to retain the catalyst support and/or catalyst in the hollow porous microspheres during the agglomeration steps and/or calcining step and will generally be removed during the calcining step.

DISPERSING AGENTS

Where slurry or sol dispersion particles, e.g. catalyst or catalyst supports are in the colloidal size range of 0.005 to 0.1 microns in size and they have an affinity for the continuous liquid phase or if they have like surface charges, they can naturally form a stable dispersion and an added dispersing agent may not be needed. Also, when the slurry or sol dispersion particles are formed in situ just before or just after the particles are deposited on or in the hollow microsphere an added dispersing agent may not be needed. However, for ease of handling and for maintaining the dispersed particles, particularly particles above 0.1 to 1.0 microns in size, in a stable slurry or sol dispersion a dispersing agent is usually added.

When the dispersed particles are smaller than about 0.005 microns the particles begin to assume the properties of a true solution. When the particles are greater than 0.1 micron there is a natural tendency for the particles to separate out of the liquid phase and a dispersing agent and/or continuous stirring of the dispersed particle composition is or are required up until just before applying the slurry or sol dispersion to the microspheres.

A sufficient amount of dispersing agent is added such that the dispersed particles form a stable dispersion for a period long enough to apply the slurry or sol dispersion to the hollow microspheres.

Dispersing agents that are suitable for use with aqueous continuous liquid phase compositions are the commercially available sodium alkyl and sodium aryl sulfonic acids. Another dispersing agent that can be used is sold under the trade name Darvan-7 which is a sodium polyelectrolyte, and is available from R. T. Vanderbilt Co., 230 Park Avenue, New York, NY 10017. Organic carboxylic acids and organic polycarboxylic acids, e.g., citric acid, can be added to maintain a desired pH, and function as dispersing agents.

Dispersing agents that are suitable for use with non-aqueous, e.g., organic solvent, continuous liquid phase compositions are generally those used in the industry, e.g., fatty acids (glyceryl tri-oleate), Menhaden Fish Oil (Type z-3, sold by Jesse Young, Co.) and the commercially available benzene sulfonic acid surfactants.

EXAMPLES

The following examples illustrate the preparation of microsphere catalysts and applications of microsphere catalysts for carrying out catalytic reactions in accordance with the present invention.

EXAMPLE 1

An auto emission control catalyst is prepared in accordance with the present invention by impregnating hollow porous microspheres containing macro pores with precious metal catalysts or mixtures thereof.

The hollow porous microspheres are prepared from an alumina dispersed particle composition following the procedure of applicant's copending application Ser. No. 639,126. The alumina particle composition contains alumina particles 0.1 to 5.0 micron in size. The dispersed particle composition also contains combustible macro particles about 100 microns in diameter. The hollow porous microspheres used are 1500 to 2000 microns in diameter and about 40-80 microns wall thickness and contain a multiplicity of macro pores about 100 microns in diameter.

The use of hollow, as distinguished from solid microspheres as the substrate for the catalyst substantially increases the heat-up rate of the catalyst bed upon engine start-up and reduces the rate at which the abutting bodies abrade catalyst from the surfaces of each other due to vibration and road shock. All of this because of the substantial reduction in the weight of the microspheres by reason of their being hollow.

The particular choice of catalytic agents used depends upon the performance characteristics desired in the system. Principally the noble metals platinum, palladium and rhodium and mixtures thereof are used in automobile exhaust emission control.

The catalyst can contain platinum alone, palladium alone, mixtures of platinum and palladium, mixtures of platinum or palladium with rhodium or mixtures of platinum and palladium and rhodium. Where the mixed catalyst comprises platinum and palladium they can be used in amounts of platinum 65-75% and palladium 25-35% by weight. Where rhodium is added to platinum or palladium, or to platinum and palladium it is added in an amount of 5-15% by weight of catalyst.

Where a mixture of platinum and palladium is used the hollow porous microspheres can be impregnated with a platinum and palladium solution generally following the procedure described in Sanchez U.S. Pat. No. 4,390,456. To prepare a suitable auto emission catalyst 2000 grams of microspheres are impregnated with a solution which is prepared as follows: $SO_2$ is bubbled into 800 ml. of deionized water for 20 minutes at 1 m. mole/minute after which about 4.2 ml. of $Pd(NO_3)_2$ solution containing 100 mg. palladium per ml. is added. The resulting solution is yellowish green indicating complexing of the palladium. A solution of ammonium platinum sulfito salt, $(NH_4)_6Pt(SO_3)_4 \cdot H_2O$, is prepared by dissolving about 4.0 g of the platinum salt having a platinum content of about 31.0% in 800 cc water. The palladium solution is then added to the platinum solution. The total volume is then increased to about about 2000 ml. by the addition of additional deionized water. The solution is then used to impregnate the microspheres by contacting the microspheres until the microspheres are saturated with catalyst solution.

The microspheres are separated from the catalyst solution and allowed to drain dry after which they are placed in an oven and dried at 300°-350° F. for one to two hours. After drying the catalyst is activated by heating at 800°-900° F. for one two to hours in air.

The hollow porous microspheres have platinum and palladium deposited on the inner and outer microsphere wall surfaces. The catalyst is also deposited in the interconnecting channel surfaces in the microsphere walls. The microsphere pores of a size of about 1.0 to 5.0 micron and the macro pores of about 100 microns size provide ready access of the combustion gases to the catalyst sites in the interconnecting voids and on the inner wall surface of the microspheres.

The microsphere catalyst can be placed in a suitable container or catalytic converter and installed in an engine exhaust line system. The catalytic converter can be designed to have a straight-through flow, a cross-flow, or a radial flow and may be used alone or in combination with a conventional type of acoustic muffler. Combustion air can be injected ahead of the converter inlet by use of an aspirator means or by an external compressive means.

At an operating temperature of the catalyst of 200° to 300° C., the CO and hydrocarbon content in an automobile exhaust are each reduced by at least 30 to 50% by volume. The CO is converted to $CO_2$ and the hydrocarbons converted to $CO_2$ and $H_2O$.

In another embodiment of the invention the hollow microspheres are first treated with a sol dispersion of alumina particles to the point of saturation. The microspheres are then heated to dry the microspheres and deposit the alumina particles as an alumina support. The alumina particles deposit on the inner and outer microsphere wall surfaces and on the surfaces of the dispersed particles that form the interconnecting channels in the microsphere walls. The microspheres are then further heated to activate the alumina support. The microspheres containing the activated alumina support are treated as described immediately above to deposit palladium and platinum catalyst on the alumina support. The microsphere catalyst are tested as before and are found to substantially reduce the hydrocarbon and CO content of an automobile exhaust stream.

In another embodiment the hollow microspheres are coated with platinum and palladium chloride solutions generally following the procedure described in Watson et al U.S. Pat. No. 4,039,480. The microspheres are impregnated with the solution after which the impregnating solution is evaporated. As the solution is evaporated, metallic salts are deposited on the inner and outer wall surfaces of the microspheres and on the surfaces of the interconnecting channels in the walls forming salt crystals. After drying the microspheres are heated at 900°-1000° C. for 1 to 2 hours in an oxidizing atmosphere to decompose the metal salts to elemental Pt and Pd. The thus prepared catalyst can be used in a catalytic converter as before.

In another embodiment of the invention where reduction of nitrous oxides in the exhaust is a primary concern, the catalyst solutions taught in the Stenzel et al U.S. Pat. No. 4,077,908 can be used to impregnate the microspheres. For example, a mixture of $Cu(NO_3)_2 \cdot 3H_2O$, $Ni(NO_2)_2 \cdot 6H_2O$ and $Mn(NO_3)_2 \cdot 4H_2O$ in solution can be used to impregnate the hollow porous microspheres. The impregnated microspheres are dried and then treated to activate the catalyst. The microsphere catalyst can be used as before for auto emission control.

The emission control catalyst in addition to being used in various vehicle exhaust systems, can be used in stationery engine systems, such as generators, auxilary power in power boats, in chemical or industrial processes in which carbon monoxide, hydrocarbons and nitrous oxides are the principal combustion product pollutants.

EXAMPLE 2

Hydrodesulfurization and/or hydrodenitrogen catalysts are prepared in accordance with the present invention by first impregnating hollow porous microspheres with an alumina support and then impregnating the hollow porous microsphere containing the alumina support with a solution containing cobalt-molybdate or a solution containing nickel-molybdate The hollow porous microspheres are used as a substrate for a cobalt-molybdenum or nickel molybdenum catalyst deposited on an alumina support.

Hollow porous microspheres are made from an alumina dispersed particle composition. The microspheres are 2000 to 4000 microns in diameter and 40 to 80 microns wall thickness. The microspheres are made in accordance with the method described in applicant's copending application Ser. No. 639,126. The hollow porous microspheres are substantially uniform in diameter and substantially uniform in wall thickness and porosity. The microspheres are examined and it is found that the microsphere walls have a 25-30% porosity and uniform distribution of interconnecting voids, and that the microspheres are rigid and have relatively high strength, requiring in excess of 500 psi at point to point contact to break the microspheres. The microsphere pores, i.e. the openings in the outer wall surface, a cross-section of the interconnecting pores and the openings on the inner wall surface are examined and are about 1 to 3 microns. If desired, the microspheres can be made to also contain macro pores 80 to 100 microns in diameter.

To prepare an alumina catalyst support an aqueous alumina sol dispersion containing an about 25 weight percent alumina particles, e.g. 12 to 17 volume percent of the sol dispersion, in the range of 0.05 to 0.1 microns in size is contacted with the hollow porous microspheres on a porous bed. A suction is applied under the bed to draw the alumina sol dispersion into the single central cavity of the microspheres and to fill the microspheres. The microspheres are dried at about 65°–100° F. and then washed to remove excess alumina sol dispersion.

The washed and dried microspheres are then gradually heated to a temperature of 260° C. to 900° C. to calcine the alumina support. The alumina particles on heating sinter together at their points of contact to form a porous latticework of alumina particles in the single central cavity, in the interconnecting voids and bridging the microsphere pores on the outer wall surface of the microspheres and the microspheres pores on the inner wall surface of the microsphere walls. The porous latticework of alumina particles made from the alumina sol dispersion comprises about 80% void content and has a pore size of up to 200 microns. The pore size measured is that between clusters of adjacent alumina particles in the latticework formed by the alumina sol dispersion. The alumina support is immobilized in the latticework and is now ready for impregnation with an active catalyst. In another embodiment, the microspheres may be subjected to vibration during drying to partially break-up the alumina support latticework. The latticework is broken up into alumina particle clusters 50 to 200 microns in size with a corresponding reduction pore diffusion resistance.

The hollow porous microspheres to be useful for hydrodesulfurization or hydrodenitrogenation should contain at least one hydrogenation agent and preferably contain a combination of two such agents. The metals and/or the metal sulfides and oxides of molybdenum and tungsten, and the metals and/or the metal oxides and sulfides of cobalt and nickel, are satisfactory hydrogenation agents. Combinations of nickel-molybdenum and nickel-tungsten are preferred for hydrodenitrification and the combination of cobalt-molybdenum is preferred for hydrodesulfurization.

The catalyst can be incorporated into the calcined support by any of the well-known methods, preferably by impregnation ordinarily employed in the catalyst preparation art.

A suitable catalyst is made by impregnation of the alumina support using a solution of a cobalt or nickel salt and phosphomolybdic acid. The cobalt or nickel content should be in the range of 2–5 parts calculated as the pure metal and the molybdenum or tungsten content should be 5–20 parts calculated as a pure metal based on weight of catalyst and alumina support. It should be understood that the metal catalyst can be present in the final catalyst in the compound form such as the oxide or sulfide form as well as the elemental metal.

The hydrodesulfurization or hydrodenitritrogenation catalysts of this invention are suitable for hydrotreating heavy hydrocarbonaceous feeds such as coal liquids or fractions resulting from the dissolution of coals, e.g. bituminous coals. Other suitable feeds for desulfurization include hydrocarbonoceous products or fractions from tar sands, shale oil and petroleum, including atmospheric or vacuum residual, topped crude, reduced crude, solvent deasphalted residual, as well as distillate material such as vacuum gas oil from petroleum, etc.

The processing of hydrocarbonaceous feed stocks according to this invention requires that the feed stock be contacted with a fixed or moving bed containing the microsphere catalyst of this invention under hydroprocessing conditions, as are well known in the art, for example those disclosed in Kyan U.S. Pat. No. 4,342,643 and MacLaren U.S. Pat. No. 2,912,375. Suitable hydroprocessing conditions include temperatures of 250° C.–450° C., pressure of from 30–200 atmospheres and hydrogen gas rates of 2000 to 12000 standard cubic feet of hydrogen per barrel of feed stock.

A microsphere catalyst containing cobalt and molybdenum on an alumina support is tested for hydrodesulfurization activity by contacting the catalyst with a California vacuum distillate gas oil containing 1.2% organic sulfur. The hydrodesulfurization conditions are temperature of about 350° C., about 30 atm. total pressure and about 6000 standard cubic feet of hydrogen per barrel of oil feed. The desulfurized product is tested and the sulfur contact is found to be substantially reduced, e.g. to a level below about 0.50 weight percent sulfur.

The hydrodesulfurization and hydrodenitrigenation processes can advantageously be carried out using the process and apparatus described in MacLaren U.S. Pat. No. 2,912,375. The MacLaren patent describes carrying out continuous desulfurization or denitrification process in a moving bed followed by a continuous catalyst regeneration step.

EXAMPLE 3

A hydrocracking catalyst is prepared in accordance with the present invention by impregnating hollow porous microspheres with a composition comprising a sol dispersion of silica particles in a solution of nickel and aluminum. The silica particles form a support for a nickel-alumina catalyst. The hollow porous microspheres are used as a container for a nickel-alumina catalyst deposited on a silica support. The hollow porous microspheres having 2000 to 4000 micron diameter and a 40 to 80 microns wall thickness are used. The microspheres can contain macro pores 40 to 80 microns in diameter.

The nickel-alumina on silica support catalyst can be prepared by generally following the method described in Kyan U.S. Pat. Nos. 4,342,643 and 3,673,079. For example, aluminum oxide is reacted with hydrochloric acid and water to form a 20% aluminum chloride solution. Nickel powder is reacted with HCl and water to form an about 30% nickel chloride solution. About five hundred eighty-six grams of aluminum chloride solution are put into a container. To this is added about 250 grams of the nickel-chloride solution and about 180 grams of glacial acetic acid. A second solution is made by diluting about 1150 grams of sodium silicate with about 2 liters of water. A dilute solution of the sodium silicate is added slowly to the first solution with stirring to form a silica sol in an aluminum and nickel chloride solution. The silica sol-nickel-aluminum solution is then used to fill the single central cavity of the hollow porous microspheres.

The filled microspheres are removed from the silica sol-nickel-aluminum solution and are contacted with a dilute aqueous ammonia solution (16.5 wt.% $NH_4OH$). The ammonia solution reacts with the nickel and aluminum to form a gel of the corresponding nickel and aluminum hydroxides. The ammonia contact is continued until a pH 7.5 is reached. The microspheres are washed to remove excess ammonia. The microspheres are then heated to a temperature of about 120° C. to remove excess water and further heated to a temperature of about 300° to 800° C. to calcine the silica-alumina and nickel catalyst.

The finished catalyst contains about 6 weight percent nickel and about 12 weight percent alumina on the silica support. The catalyst is suitable for hydrocracking hydrocarbonaceous feeds to produce lower boiling materials. Suitable feed stocks for hydrocracking include distillates such as vacuum gas oil and metal containing distillates from petroleum, coal-derived liquids, and hydrocarbonaceous materials from tar sands and shale oils. Hydrocracking is also performed on residual petroleum feed stocks such as atmospheric and vacuum residual fractions.

Alternatively, the ammonia treating step can be omitted and the microspheres dried and heated to precipitate the catalyst. The nickel and aluminum precipitate on a silica latticework as nickel oxide and alumina ($Al_2O_3$). The silica during the drying and calcining step forms a highly porous latticework of silica particles in the single central cavity of the microsphere with the nickel oxide and alumina deposited thereon.

The microsphere catalyst can be used to carry out hydrocracking processes under conventionally used hydrocracking process conditions, for example, the conditions disclosed in Price, et. al., U.S. Pat. No. 3,159,568 of temperatures of about 650° to 850° F. (343° to 454° C.), pressures of about 500 to 2000 psig, hourly space velocities of about 0.5 to 8.0 volumes of liquid feed per volume of catalyst and hydrogen ratios of about 500 to 15000 standard cubic feet of hydrogen per barrel of hydrocarbon feed.

EXAMPLE 4

A molecular sieve catalytic cracking catalyst is prepared in accordance with the present invention using hollow porous microspheres as containers for 13Y crystalline zeolite molecular sieve catalyst. The hollow porous microspheres are made following the procedure described in applicant's copending application Ser. No. 639,126.

Hollow porous microspheres are made from an alumina dispersed particle composition. The microspheres are 2000 to 4000 microns in diameter and 40 to 60 microns wall thickness. The dispersed particle composition used to make the hollow porous microspheres contains about 2–4 volume percent of vaporizable macro particles about 60 to 80 microns in size. The hollow porous microspheres contain a multiplicity of macro pores about 60 to 80 microns in diameter. The microsphere pores are about 1–3 microns and the microspheres have a wall porosity or void content of about 30–35%.

A 40–60 weight percent slurry of Na-13Y zeolite molecular sieve is prepared from a finely divided Na-13Y zeolite crystalline powder. The Na-13Y zeolite crystals are 1–10 microns in size and have a pore size of about 0.7 to 0.9 nm (0.0007 to 0.0009 microns). The hollow porous microspheres, in a layer one to three microspheres deep, are placed on a porous moving belt and a suction is applied to the bottom side of the porous belt. The slurry of Na-13Y zeolite is sprayed onto the microspheres to saturation. The suction applied beneath the porous belt causes the slurry to fill the single central cavity of the microspheres. The slurry passes into the central cavity primarily through the macro pores entrance means in the microsphere wall. After the microspheres are filled with the slurry, the microspheres containing the Na-13Y zeolite slurry are treated to remove the carrier vehicle. This step causes sufficient agglomeration of the Na-13Y sieve crystals such that the crystals are not easily removed from the single central cavity of the hollow microspheres. The carrier vehicle used to form the slurry can be organic or inorganic and will have a low solubility for the zeolite.

The hollow porous microspheres containing the Na-13Y sieve crystals are then treated to cation to exchange the Na for the lanthanum series rare earth elements, e.g. lanthanum, cerium, praseodymium, neodymium, promethium, samarium, europium and gadolinium. The cation exchange of the Na for lanthanum series rare earth elements to make cracking catalyst is well known and conventional in the art. The rare earth cation exchange is carried out for a sufficiently long period that all or substantially all the sodium cation is removed. After the rare earth cation exchange reaction is completed the microsphere containing the rare earth 13Y-zeolite is heated to dry the molecular sieve and to further agglomerate the zeolite crystals to a size such that the crystals do not come out of the macro pores. The microsphere catalyst can be further treated as in conventional in the art to activate or otherwise prepare the catalyst for use in a catalytic cracking process.

The microsphere catalyst containing the rare earth-Y zeolite catalyst is effectively a binderless pellet. The hollow porous microsphere provides a strong protective porous outer shell which protects the crystalline zeolite from attrition while the crystalline zeolite without the conventionally used diffusion limiting binder material can more effectively and efficiently carry out the desired catalyst reaction.

In zeolites the catalysis takes place within the intracrystalline void structure of the zeolites. The catalytic reaction takes place at the active catalyst sites by diffusion of reactants to the sites and products from the sites.

In the prior art catalyst, the binder used to form pellets affect the catalytic reactions because of the need of reactants and products to diffuse into and out of the binder used to form the pellets. The ability to form a catalyst without the use of a binder substantially increases the diffusion of reactants and products into and out of the crystalline zeolite structure.

The microsphere catalyst containing rare earth Y-zeolite offer the advantages of high strength, high attrition resistance, high rates of inter molecular hydrogen transfer coupled with extremely high intrinsic cracking activity and the high thermal stability of the zeolite cracking catalyst.

The rare earth Y-zeolite microsphere catalyst can be used to crack hydrocarbon petroleum fractions in conventional cracking processes, e.g. fixed or moving bed processes in a mixture with conventional silica-alumina cracking catalyst, to increase the yield of light cycle oil, the yield and octane of the gasoline product fraction, and decrease the production of coke. The high cracking rates that are obtained with the zeolite catalyst results in greatly reduced contact times for given conversion levels, thus further increasing liquid-product yields. An additional advantage obtained with the zeolite catalyst contained in the hollow microsphere is greater operating flexibility.

The catalytic cracking process conditions that can be used are conventional in the art, for example, temperatures of about 300° to 600° C. and pressures of about 30 psia to 200 psia.

The Na-13Y and Na-13X crystalline molecular sieve zeolites can also be cation exchanged with magnesium, calcium or zinc, or with $NH_4^+$ and conversion to the acid form. These catalyst can be used as hydrocracking catalyst. The hydrocracking process conditions that can be used are conventional, for example, those disclosed in Price, et. al., U.S. Pat. No. 3,159,568 of temperatures of about 450° to 700° F. (232° to 371° C.) and pressures of about 500 to 1500 psig.

EXAMPLE 5

The hollow porous microspheres of the present invention are used in a two step process to treat stack gas from a coal fired or oil fired electric power generating station to selectively remove and recover $SO_2$ from the stack gas and to convert nitrogen oxides ($NO_x$) in the stack gas to nitrogen ($N_2$).

In the first step of the process the stack gas is contacted with hollow porous microspheres containing finely divided molecular sieve carbon particle catalyst having a large surface area to catalytically convert the $SO_2$ to $H_2SO_4$ and to catalytically reduce the nitrogen oxides to nitrogen. The $H_2SO_4$ is adsorbed by the carbon catalyst. The carbon catalyst containing the adsorbed $H_2SO_4$ is heated and a gas stream containing concentrated $SO_2$ and $CO_2$ is desorbed.

In the second step of the process the concentrated $SO_2$ and $CO_2$ gas stream is contacted with hollow porous microspheres containing an absorbent which is a selective solvent for $SO_2$, e.g. polyethylene glycol (PEG). The polyethylene glycol has a high selectivity and high solubility for $SO_2$ over $CO_2$. The $SO_2$ and $CO_2$ gas stream is contacted at elevated pressure with the microspheres containing the polyethylene glycol absorbent particles and the $SO_2$ is selectively dissolved in the polyethylene glycol. On reducing the pressure to about atmosphere pressure the $SO_2$ comes out of solution in the polyethylene glycol, is separated, repressurized and is recovered as liquid $SO_2$ product.

The hollow microspheres of the present invention allow the use of materials as catalyst, adsorbents, absorbents or solvents which heretofore could not be used as effectively as catalyst, adsorbents, absorbents or solvents. This is accomplished by encapsulating the catalyst, adsorbents, absorbents or solvents within the single central cavity of the hollow porous microspheres. Where the catalyst, adsorbent, absorbent or solvent is a liquid, a thickener is added to the liquid to form an immobilized liquid membrane or coating on and/or in the hollow microsphere.

Heretofore the use of finely divided carbon particles as catalysts or sorbents had been restricted because the particles were weak structurally, had high attrition rates and were elutriated from the process. There was also the risk of combustion of the finely divided carbon particles during regeneration of the carbon catalysts or sorbent.

In prior uses of finely divided molecular sieve carbon particles, for example, in the "char" process, degradation of the carbon particles occurred because of weakening and attrition of the particles due to expansion of the particles during repeated adsorption and desorption cycles. The combustability of the carbon particles during the high temperature regeneration, i.e. desorption cycle also causes degeneration of the carbon particles. It was also found that there was an increase in size of the carbon pores and a corresponding decrease in physical strength of the carbon particles due to continuous adsorption and desorption cycles which lead to weakening and the ultimate disintegration of the carbon particles.

The encapsulation of the finely divided molecular sieve carbon particles catalyst within the single central cavity of the hollow porous microspheres in accordance with the present invention protects the carbon particles from attrition, reduces the contact of the carbon particles with combustion gas, i.e. oxygen in the process stream, and generally protects the carbon particles during the process adsorption and desorption cycles. The entrance means, i.e. the microsphere pores and macro pores will not admit oxygen to the central cavity of the microspheres at a sufficient rate to support gross combustion of the carbon particle catalyst.

The polyethylene glycol, though having a high solubility and selectivity for $SO_2$ when used in thin films or in finely divided form, has a tendency to become soft and sticky in use when subjected to modest body force pressures. The polyethylene glycol's general lack of structural integrity has prevented its use as a selective solvent in large scale commercial processes for the selective removal of SO$_2$.

The present invention in which hollow porous microspheres are used to encapsulate the finely divided molecular sieve carbon particle catalyst or the polyethylene glycol selective solvent uncouples the requirement of selective catalytic activity of the carbon catalyst and the selective solubility of the polyethylene glycol from the requirements of high mechanical strength and structural integrity.

Encapsulation of Carbon Particles

Hollow porous alumina particle microspheres are prepared and have a 2000 to 4000 microns diameter, a 60 to 80 microns wall thickness, a 25 to 35% porosity (in the walls) and macro pores 60 to 80 macrons in size. The macro pores are selected to be about the same size as the thickness of the walls of the microspheres. The microsphere pores in the walls of the microspheres are about 1 to 3 microns in size.

A batch of the hollow porous microspheres are filled with a conventional carbon molecular sieve precursor material. The hollow microspheres containing the precursor material are then heated in a manner known in the art to convert the precursor material to carbon molecular sieve catalyst. The carbon particles are examined and are found to have a carbon particle pore size of 4 to 9 angstroms, with a narrow pore size distribution. Alternatively, the carbon molecular sieve catalyst can be formed, a slurry of the carbon catalyst made and the microspheres filled through the macro pores with the carbon molecular sieve catalyst. The microspheres are then treated to remove the carrier from the slurry.

It is found that the finely divided carbon particles do not come out through the microsphere pores or macro pores entrance means because the particles have a small affinity for each other and form loose agglomerates of carbon particles. The loose agglomerates are not subject to stresses due to their neighbors because they are confined within the microsphere central cavity. These loose agglomerates can reach a size of 100 to 200 microns which also prevents them from coming out through the macro pores of the microspheres.

The method of making finely divided molecular sieve carbon particle catalyst is well known in the art. The carbon molecular sieves can be prepared by the decomposition of a wide variety of starting materials, including pitch and saran. The molecular sieve carbon structure obtained is dictated by the controlled cracking and controlled partial gasification of the hydrocarbons contained within the hollow microspheres. A discussion of how the molecular sieve carbon particle catalyst are made is contained in D. L. Trimm, Methods of Preparation of Carbon Molecular Sieves, Carbon No. 15, 273 (1977).

Since the molecular sieve carbon particles are formed by decomposition of a hydrocarbon, e.g. pitch, to essentially carbon, the carbon particles remaining in the central cavity after decomposition will usually fill only about one third to one half of the central cavity. Additional filling of the central cavity can be accomplished by repeating the cycle.

The hollow microspheres, partially filled with carbon catalyst, can be stacked in a tower in the form of a fixed or moving bed, as schematically illustrated in FIG. 9 of the drawings. The carbon catalyst within the hollow microspheres can form a loose bed. "Ebulliation" can be practiced to actually cause a stirring of the loose bed of carbon particles inside of each microsphere. The diameter and densities of the microspheres and the reactant fluid stream velocities can be adjusted such that the microspheres are almost floating in an upwardly moving reactant fluid stream. This can cause a jiggling which would reduce the path length of diffusion of a reactant into and out of contact with the catalyst in the central cavity of the microsphere.

Encapsulation of Polyethylene Glycol

The hollow porous microspheres having macro pores are made from an alumina dispersed particle composition in accordance with the method described in applicant's copending application Ser. No. 639,126. The microspheres are 2000 to 4000 microns in diameter and 60 to 80 microns wall thickness. The microspheres are substantially uniform in diameter and substantially uniform in wall thickness and porosity. The microspheres have a 25–30% porosity and uniform distribution of interconnecting voids, are rigid and have relatively high strength. The microsphere pore openings are 1 to 3 microns. The microspheres have a plurality of macro pores 80 to 100 microns in diameter.

In order to increase the absorption capacity of the microspheres for $SO_2$, the microspheres are treated with an alumina sol to fill the hollow central cavity of the microspheres with a porous alumina support. The hollow porous microspheres containing the alumina support are then impregnated with a composition to deposit on the microsphere and alumina support an immobilized liquid membrane absorbent that is selective to $SO_2$. The hollow porous microspheres and contained alumina support are used as a substrate for the immobilized liquid membrane absorbent.

The alumina support is prepared by contacting and impregnating the hollow porous microspheres with an aqueous alumina sol dispersion containing an about 25 weight percent alumina particles, e.g. 12 to 17 volume percent of the sol dispersion. The size of the alumina particles in the sol dispersion are 0.05 to 0.1 microns. The hollow porous microspheres are placed on a porous bed and the alumina sol dispersion is applied to the microspheres. A suction is applied under the bed to draw the alumina sol dispersion into the single central cavity of the microspheres and to fill the microspheres. The microspheres are dried at about 65°–100° F. and then washed to remove excess alumina sol dispersion. The microspheres containing the dried alumina sol are heated to a temperature of 260° C. to 900° C. to sinter the alumina sol particles. The alumina sol particles on heating sinter together at their points of contact to form a porous lattice work of alumina particles. The porous lattice work of alumina sol particles form in the single control cavity and in the interconnecting voids and bridging the microsphere pores in the microsphere walls. The macro pores that are 80 to 100 microns in diameter remain open. The porous lattice work of alumina particles made from the alumina sol dispersion comprise about 80% void content and has a pore size of up to 200 microns. The pore size measured is that between clusters of adjacent alumina particles in the lattice work formed by the alumina sol dispersion. The alumina particles forming the lattice work is now ready for impregnation and coating with an immobilized liquid absorbent. If desired, the microspheres may be subjected to vibration during drying to partially break-up the alumina support lattice work. The lattice work can be broken up into alumina particle clusters 50 to 200 microns in size with a corresponding reduction pore diffusion resistance.

An immobilized liquid selective polyethylene glycol absorbent membrane coating for the hollow porous microspheres and alumina lattice work support contained in the single central cavity of microspheres can be prepared by generally following the procedure described in the W. J. Ward III and C. K. Neulander, Final Report Contract No. PH-36-68-76, General Electric Research and Development Center, Scenectady, N.Y., March 1970.

To immobilize a liquid solvent thickening agents such as hydroxyethyl cellulose, hydroxymethyl cellulose and finely divided silica or alumina particles and/or mixtures thereof can be used. To inhibit oxydation of the polyethylene glycol an anti-oxidant can be added, e.g. Ionox-330 available from Shell Chemical Co. Suitable polyethylene glycol materials which exhibit a high selectivity and high solvent capacity for $SO_2$ are Carbowax 600 and Carbowax 4000 available from Union Carbide Company.

The hollow microspheres are treated with a mixture comprising polyethylene glycol, thickening agents and an anti-oxidant. The mixture is prepared by dissolving about 6 grams of Carbowax (PEG) 4000 in 80 ml. of water, dispersing about 1.2 grams of Cabosil HS-5, a fine grade of silica marketed by Cabot Corporation, in 50 ml water and blending the Carbowax solution with the Cabosil dispersion. About one gram of Cellosize (HEC) QP-100M, marketed by Union Carbide Company, is dissolved in 200 ml. of water and blended into the polyethylene glycol and silica mixture. Optionally about 0.1 to 0.3% Ionox-330 anti-oxidant, based on weight of PEG is added to the mixture. The resulting mixture contains about 1.8% PEG, 0.35% silica and 0.3% HEC.

A batch of the hollow porous microspheres containing the alumina support are placed in a thin layer on a bed. The microspheres are sprayed to the point of saturation with the above prepared polyethylene glycol mixture. The spraying step is repeated until the microspheres are substantially filled with polyethylene glycol mixture. Alternatively, the microspheres can be immersed in a container containing the polyethylene glycol mixture and if necessary pressure applied to the mixture to assist filling the microspheres with the mixture.

The microspheres filled with the polyethylene glycol mixtures are separated and dried to remove water.

The dried microspheres have coated on the inner and outer microsphere wall surfaces and have coated on the alumina support lattice work contained in the single central cavity of the microsphere a thin polyethylene glycol immobilized liquid membrane about 2 to 10 microns thick. The macro pores remain open to allow access of the $SO_2$ gas to be absorbed to the polyethylene glycol membrane coated on the alumina support in the microsphere. If desired the thickness of the polyethylene glycol membrane coating can be increased by repeating the coating cycle.

The encapsulation of the polyethylene glycol absorbent in the hollow microspheres prevents it, during the $SO_2$ absorption process cycles from fusing together into large masses.

$SO_2$ Separation Process.

The stack gas from a coal fired electric power generation plant is treated in accordance with the present invention to remove and recover $SO_2$ and to convert nitrogen oxides to nitrogen. The conversion of the nitrogen oxides to nitrogen is considered to be of particular importance in view of recent concern that nitrogen oxides may be a significant factor in deforestation. The stack gas at a temperature of about 200° F. (93.3° C.) and containing about 0.2% $SO_2$ by volume is contacted up flow through a moving bed reactor containing the hollow porous microspheres catalyst. The hollow porous microspheres contain finely divided molecular sieve carbon particle catalyst. The hollow microspheres in contact with stack gas are circulated at a rate of approximately one to two pounds of the carbon molecular sieve catalyst per minute per $MW_e$ per percent sulfur in the coal.

The catalytic reaction for the conversion of $SO_2$ in the stack gas to $H_2SO_4$ is: $2SO_2+O_2+2H_2O \rightarrow 2H_2SO_4$.

The $H_2SO_4$ and part of the $CO_2$ in the stack gas are adsorbed by the finely divided carbon catalyst.

A catalytic reaction for the conversion of nitrogen oxides ($NO_x$) in the stack gas to nitrogen is: $2CO+2NO \rightarrow N_2+2CO_2$. The following reaction may also occur: $C+CO_2+2NO \rightarrow 2CO_2+N_2$.

As mentioned above, the $H_2SO_4$ and some $CO_2$ are adsorbed by the carbon molecular sieve catalyst. The effluent gas is essentially free of $SO_2$ and $NO_x$ and contains primarily $CO_2$, $N_2$, $H_2O$ and $O_2$ all of which are non-polluting.

The microspheres containing the carbon molecular sieves and adsorbed $H_2SO_4$ and $CO_2$ are conveyed to a regenerator vessel in which they are directly contacted with a moving bed of hot sand in a manner simiar to that used in the existing "char" process. The hot sand in direct contact with the microspheres heats the carbon molecular sieves to a temperature of about 1200° F. (648.8° C.) and converts the adsorbed $H_2SO_4$ to $SO_2$ and $H_2O$ which are desorbed from the molecular sieve carbon catalyst together with the adsorbed $CO_2$.

After the carbon catalyst regeneration step the microspheres are cooled to a temperature of about 200° F. (93.3° C.) and are recycled to the catalytic conversion and adsorption step.

A gas stream comprising about 50% by volume $SO_2$, 25% $CO_2$ and 25% $H_2O$ is off gassed from the regenerator vessel. The gas stream is cooled to a temperature of about 180° F. (82.3° C.) and compressed to 100 psia. The $H_2O$ condenses and is removed and the gas stream containing $SO_2$ and $CO_2$ is contacted in an up flow adsorption tower with a fixed stacked bed of the hollow microspheres containing a thin coating of polyethylene glycol.

The polyethylene glycol coating exibits about 35/1 selectivity to $SO_2$ over $CO_2$. The non adsorbed $CO_2$ and any remaining $H_2O$ are exhausted to the atmosphere.

The adsorption tower is cooled to 80° F. (26.7° C.) and the pressure is reduced to about 30 psia (atmospheric) and the $SO_2$ dissolved in the polyethylene glycol comes out of solution, i.e. is desorbed as essentially pure $SO_2$.

The desorbed $SO_2$ is compressed to liquify the $SO_2$ to obtain liquid $SO_2$ product.

EXAMPLE 6

The microsphere catalyst can be treated as described below to obtain microsphere catalyst with an inorganic immobilizing membrane of controlled micro pore size.

Microsphere catalyst can have microsphere pores of, for example, 1 to 3 microns and macro pores of, for example, 60 to 80 microns in diameter.

The microspheres are collected and are contacted with a stable 50 weight percent colloidal particle size silica sol dispersion in water. The silica particles are about 0.05 to 0.1 microns in size and comprise about 25 to 35 volume percent of the sol. A positive pressure is applied above the liquid level of the silica sol to force the silica sol into the interconnecting voids in the walls of the hollow porous microspheres to form a layer of sol dispersion to a depth of about one fourth to one third of the thickness of the microsphere walls (see FIG. 6), e.g. 15 to 25 microns.

The microspheres are then cleaned, dried and heated to a temperature of about 1000° to 1200° C., i.e., below the melting temperature of the silica particles, for sufficient time to sinter the silica particles and to remove the water from the silica particles. The sintered silica particles form a latticework of particles in the interconnecting voids in the microsphere walls to the depth the sol penetrates into the microspheres' walls. The removal of the continuous liquid phase and the firing and sintering of the sol dispersion results in a slight shrinkage in the thickness of the layer of the sol dispersion in the microspheres' walls.

The silica particles at the points at which they are in contact with the alumina particles that form the surfaces of the interconnecting voids are partially dissolved into or sintered to the silica particles.

The sintered silica particles comprise a strong lattice work of porous silica particles with pores of a controlled about 0.10 to 0.50 micron size, i.e., with micro pores. Particles of colloidal size, other than silica particles, for example alumina particles can be used in the manner described to form the micro pores.

EXAMPLE 7

The present invention can be used to accomplish a selective separation of a particular constituent of a reactant stream, either liquid or gas, in such a manner as to have only the selected constituent reach a specific catalyst contained within the central cavity of the hollow porous microspheres of the present invention. This is accomplished by impregnating and/or filling the microspheres with the desired catalyst then coating the microsphere with an inorganic selective membrane.

A desired catalyst is first placed in the central cavity of the microspheres and/or impregnated in the interconnecting voids and on the inner wall surfaces of the walls of the microspheres.

The microspheres can contain microsphere pores of about 1 to 3 microns in diameter. In situations where the microsphere pores are much larger a temporary substrate, e.g. of an organic polymer material can be provided on which to deposit the inorganic selective membrane precursor material. The temporary organic substrate is removed on heating to sinter the inorganic membrane.

Hollow porous alumina particle microspheres are prepared having a 2500 to 3000 micron diameter, a 40 to 60 micron wall thickness and a 1 to 3 micron microsphere pore size. The microspheres are treated to fill the single central cavities with a desired catalyst.

The microspheres are then treated to deposit on their outer wall surfaces a thin inorganic selective membrane. An inorganic selective alumina membrane having uniform pore size of about 2.5 to 5.0 nm (0.0025 to 0.0050 microns) can be deposited on the microsphere walls. The membrane is applied by spray coating the microspheres with an aqueous boehmite (gamma-A100H) sol dispersion. The boehmite sol is prepared generally following the procedure described in Leenaars et al, Journal of materials Science 19, pages 1077-1088 (1984) as briefly discussed below.

The boehmite (gamma-A100H) sol is prepared by adding aluminum secondary butoxide to water which is heated to a temperature above 80° C., e.g. about 85° C. and stirred. Two liters of water are used per mole of butoxide. The solution is kept at about 90° C. and about ½ to 1 hour after addition of the butoxide, 0.07 mole $HNO_3$ per mole alkoxide is added to peptize the sol particles. The sol is kept boiling in the open reactor for 2-3 hours to evaporate most of the butanol and is subsequently kept at 90°-100° C. for about 16 hours under reflux conditions.

The sols, as mentioned above, are then sprayed onto the microspheres. The sol fills the outer pore openings of the microspheres and the interconnecting voids of the microspheres to deposit a layer of sol 10-20 microns thick.

The microspheres are then heated to dry the sol and convert the sol to a gel. The microspheres are further heated and the temperature gradually increased to 400°-900° C. to sinter the alumina particles in the gel. The deposited layer shrinks slightly during sintering due to the removal of water to a thickness of about 6-12 microns. The sintered alumina film can have a model pore size of about 2.5-5.0 nm and a porosity of about 40 to 50%. The thin alumina film is supported by the surfaces of the interconnecting voids in the microsphere walls. The micropores of 2.5-5.0 nm are examined and are found to have a narrow size distribution.

The microsphere catalyst can be used to carryout processes in which selected reactants having molecular size less than about 2.5 to 5.0 nm are allowed to enter the microsphere central cavity, contact the catalyst and to react. Reactant constituents having a molecular size larger than about 2.5 to 5 nm are excluded from entering the microsphere central cavity and are prevented from contacting the catalyst.

A microsphere catalyst containing deposited on its outer wall surface an inorganic selective membrane can thus be used to combine in a single process step the selection of a specific constituent of a reactant stream and the catalytic reaction of the selected constituent. Because the selective membrane is inorganic the microsphere catalyst can be used at relatively high temperatures under relatively severe reaction medium conditions.

EXAMPLE 8

The microsphere catalysts prepared in accordance with the present invention can be treated to impregnate the porous microsphere wall with an organic selective semipermeable membrane. The organic selective semipermeable membrane is used in applications in which the catalytic reaction is carried out at a relatively low temperature, e.g. below 300° C. and preferably below 200° C.

The use of the organic selective semipermeable membrane allows a selective separation process to be combined with a catalytic reaction process.

The hollow porous microspheres are treated to impregnate the microsphere with a desired catalyst or the microspheres are treated to fill the central cavity of the microspheres with the desired catalyst.

A microsphere, e.g. having a diameter of about 2500 microns and a wall thickness of about 40 to 50 microns with entrance means (macro pores) of about 40 to 50 microns in diameter extending through the wall, and an average microsphere pore diameter of about 1–3 microns is used.

Following the teachings of applicant's copending application, Ser. No. 657,090, filed Oct. 3, 1984 an organic selective semipermeable membrane is applied to the porous wall of the microsphere catalyst.

After the impregnation or filling the microspheres with catalyst and after activation of the catalyst the microspheres are cleaned and dried. The microspheres are then transferred to a beaker containing 150 ml of solution comprising one part of a 2% 2(cyclohexylamino) ethane sulfonic acid solution in 0.6% NaCl (isotonic, pH=8.2) diluted with 20 parts 1% $CaCl_2$. After a 3 minute immersion, the microspheres are washed twice in 1% $CaCl_2$.

The microspheres are then transferred to a solution comprising 1/80 of one percent polylysine (average MW 35,000 AMU) in an aqueous saline solution. After 3 minutes, the polylysine solution is decanted. The microspheres are then washed with 1% $CaCl_2$, and then suspended for 3 minutes in a solution of polyethyleneimine (MW 40,000–60,000) produced by diluting a stock 3.0% polyethyleneimine solution in morpholino propane sulfonic acid buffer (0.2M, pH=6) with sufficient 1% $CaCl_2$ to result in a final polymer concentration of 0.10%. The resulting microspheres have permanent semipermeable membranes extending across the macro pores and microsphere pores at the exterior wall surface. The resulting microsphere catalyst are then washed twice with 1% $CaCl_2$, twice with an aqueous saline solution, and mixed with 100 ml of a 0.12 percent alginic acid solution. The microsphere catalysts resist clumping and contain an active catalyst.

Under microscope examination, a cross-section of the microsphere walls are found to have an appearance illustrated in FIGS. 4 and 7 of the drawings. The microspheres comprise an ultrathin membrane 44 (FIG. 4) and 50 (FIG. 7) extending within and across the macro pores (FIG. 4) and microsphere pores (FIG. 7) near the periphery of the microsphere walls. The catalyst contained within the microspheres are isolated from chemicals having a larger molecular size than the size that can permeate through the organic selective semi-permeable membrane. However, reactant molecules having a molecular size small enough to permeate through the membrane can transverse membrane 44 into central cavity 50. This allows reactants to reach the catalyst contained in the microsphere and allows products to be removed from the single central cavity into the surrounding reaction medium.

The organic selective semipermeable membrane can be made from other conventional organic membrane materials and the particular material is selected to have the desired permeation or diffusion properties.

The catalyst selected to be encapsulated can be any of the conventional catalyst to carryout a desired catalyst reaction. Obviously the organic semipermeable membrane must allow permeation or diffusion of the reactant to reach the catalyst and the catalyst reaction must be carried out at temperatures sufficiently low such that the organic selective semipermeable membrane is not altered or damaged during the catalyst reaction.

The rigid walls of the microspheres provide all the required structural support for and protect the semipermeable membrane and catalyst from shearing forces and mechanical damage. Therefore, the semipermeable membranes can be substantially thinner than in conventional semipermeable membrane systems wherein the membranes also provide the structural support. This allows the microsphere catalyst to be used at much larger packing densities, in long columns, and in fixed, moving bed or fluidized bed processes.

UTILITY

The catalysts that are used are those that are conventionally used in the industry and can be added to the microspheres or microspheres and catalyst support in the form of solutions, sols, slurries or melts. The catalyst can be added to the microspheres or microspheres and support by coating the outer wall surface of the microspheres, impregnating the interconnecting voids in the walls of the microspheres, coating the interior wall surfaces of the microspheres and can be used to fill or partially fill the single central cavity of the microspheres. The catalysts or catalyst supports can be formed in situ in the walls or in the single central cavity. The catalysts can be activated or calcined in the manner conventional in the art.

The inorganic selective membranes or the organic selective semipermeable membranes that can be used to coat or impregnate the walls of the microspheres are those conventionally used in the art to carryout selective separations. The distinction, however, is that the membranes can be used in thickness of about 0.1 to 20 microns, preferably 0.5 to 5.0 microns, since the strength is supplied by the rigid wall of the hollow porous microsphere.

The microsphere catalyst of the present invention can be used to carryout a wide variety of catalytic reactions.

These and other uses of the present invention will become apparent to those skilled in the art from the foregoing description and the appended claims.

It will be understood that various changes and modifications may be made in the invention, and that the scope thereof is not to be limited except as set forth in the following claims.

I claim:

1. Hollow porous microsphere catalysts of substantially uniform diameter of 200 to 10,000 microns and of substantially uniform wall thickness of 1.0 to 1000 microns, the walls of said microspheres comprise sintered together particles which define interconnecting voids within the walls and a single central cavity in the interior of the microspheres and inner and outer microsphere wall surfaces, said interconnecting voids are continuous and extend from the outer wall surface to the inner wall surface, said walls have substantially uniform void content and said interconnecting voids are substantially uniformly distributed in the walls of the hollow microspheres, said walls include entrance means through which catalyst can be introduced into the interconnecting voids and into the single central cavity of the microspheres, said microspheres have catalyst on the particles forming the walls or have catalyst contained within the single central cavity or have catalyst on the particles forming the walls and have catalyst contained within the single central cavity, and the walls of said microspheres are free of latent solid or liquid blowing gas materials and are substantially free of relatively thinned wall portions or sections and bubbles.

2. The microsphere catalyst of claim 1 wherein the walls of said microspheres comprise sintered together inorganic particles.

3. The microsphere catalyst of claim 1 wherein catalyst is on the particles forming the interconnecting voids and on the particles forming the inner wall surface of the microsphere walls.

4. The microsphere catalyst of claim 1 wherein the catalyst is contained within the single central cavity in the interior of the microsphere.

5. The microspheres catalyst of claim 1 wherein the microspheres are of substantially uniform diameter of 500 to 6000 microns and are of substantially uniform wall thickness of 5 to 400 microns.

6. The microspheres catalyst of claim 5 wherein the microspheres are of substantially uniform diameter and of substantially uniform wall thickness and are substantially spherical in shape.

7. The microspheres catalyst of claim 1 wherein the microspheres are rigid.

8. The microspheres catalyst of claim 1 wherein the walls of said microspheres comprise sintered together ceramic particles and the microspheres are of substantially uniform diameter of 500 to 6000 microns and are of substantially uniform wall thickness of 5 to 400 microns.

9. The microspheres catalyst of claim 1 wherein the walls of said microspheres comprise sintered together alumina particles and the microspheres are of substantially uniform diameter of 500 to 6000 microns and are of substantially uniform wall thickness of 5 to 400 microns.

10. The microspheres catalyst of claim 1 wherein the walls of said microspheres comprises sintered together glass particles and the microspheres are of substantially uniform diameter of 500 to 6000 microns and are of substantially uniform wall thickness of 5 to 400 microns.

11. The microsphere catalyst of claim 1 wherein the walls of said microspheres comprise sintered together metal particles and the microspheres are of substantially uniform diameter of 500 to 6000 microns and are of substantially uniform wall thickness of 5 to 400 microns.

12. The microspheres catalyst of claim 1 wherein the walls of said microspheres comprise sintered together metal glass particles and the microspheres are of substantially uniform diameter of 500 to 6000 microns and are of substantially uniform wall thickness of 5 to 400 microns.

13. The microspheres catalyst of claim 1 wherein the walls of said microspheres comprise sintered together plastic particles and the microspheres are of substantially uniform diameter of 500 to 6000 microns and are of substantially uniform wall thickness of 5 to 400 microns.

14. The microspheres catalyst of claim 1 wherein the void content of the walls of the microspheres comprises 5 to 45 percent by volume of the microsphere wall.

15. A mass of the microspheres catalyst of claim 1.

16. The microspheres catalyst of claim 1 containing distributed in the walls of said microspheres macro pores which are 1 to 1000 microns in size and which extend through the microsphere walls.

17. The microsphere catalysts of claim 5 containing distributed in the walls of the microspheres macro pores which are 5 to 400 microns in size and which extend through the microsphere walls.

18. The microspheres catalyst of claim 2 wherein the microspheres are of substantially uniform diameter of 1200 to 6000 microns and are of substantially uniform wall thickness of 10 to 200 microns.

19. The microsphere catalyst of claim 18 containing distributed in the walls of the microspheres macro pores which are substantially uniform in size and are 10 to 200 microns in size and which extend through the microsphere walls.

20. The microsphere catalyst of claim 2 wherein the microsphere walls contain voids and the void content of the walls of the microspheres comprise 15 to 35 percent by volume of the microsphere walls.

21. The microsphere catalyst of claim 1 wherein the ratio of wall thickness to outer diameter is 1:4 to 1:500.

22. The microsphere catalyst of claim 5 wherein the ratio of wall thickness to outer diameter is 1:10 to 1:300.

23. The microsphere catalyst of claim 18 wherein the ratio of wall thickness to outer diameter is 1:10 to 1:300.

24. The microsphere catalyst of claim 1 wherein the sintered together particles have a particle size in the range of 0.1 to 60 microns.

25. The microsphere catalyst of claim 1 wherein the entrance means in the microsphere walls is comprised of microsphere pores in the walls of the microspheres having an average diameter in the range of from about 0.1 to 10 microns.

26. The microsphere catalyst of claim 2 wherein the microspheres can withstand two point contact pressures of about at least 100 psi.

27. The microsphere catalyst of claim 1 comprising a catalyst support on the sintered particles forming the microsphere walls, or a catalyst support within the single central cavity, or a catalyst support on the particles forming the microsphere walls and a catalyst support within the single central cavity, and a catalyst on said catalyst support or catalyst supports.

28. The microsphere catalyst of claim 2 wherein the microsphere walls contain entrance means and there is contained in the entrance means an inorganic selective membrane.

29. The microsphere catalyst of claim 2 wherein the microsphere walls contain entrance means and there is contained in the entrance means an organic selective semipermeable membrane.

30. The microsphere catalyst of claim 1 wherein there is contained in the entrance means an inorganic or organic immobilizing membrane.

31. The microsphere of claim 1 wherein the catalyst is deposited from a solution, slurry, sol dispersion or melt.

32. The microsphere catalyst of claim 2 wherein the microsphere catalyst has a single central cavity and the catalyst is contained within the single central cavity and the catalyst is in the form selected from the group of finely divided solid particles, finely divided resin particles and a gel.

33. A method of making hollow microsphere catalysts which comprises applying a catalyst to hollow porous microspheres of substantially uniform diameter of 200 to 10,000 microns and of substantially uniform wall thickness of 1.0 to 1000 microns, the walls of said microspheres comprise sintered together inorganic particles which define interconnecting voids within the walls and a single central cavity in the interior of the microspheres and inner and outer microsphere wall surfaces, said interconnecting voids are continuous and extend from the outer wall surfaces to the inner wall surfaces, said walls have substantially uniform void content and said interconnecting voids are substantially uniformly distributed in the walls of the hollow microspheres, said walls include entrance means through which catalysts can be introduced into the interconnecting voids and into the single central cavity of the microspheres, and the walls of said microspheres are free of latent solid or liquid blowing gas materials and are substantially free of relatively thinned wall portions or sections and bubbles, and said catalyst is applied to the particles forming the walls of the microspheres, is placed within the single central cavity of the microspheres or is applied to the particles forming the walls and is placed within the single central cavity of the microspheres.

34. The method of claim 33 wherein the catalyst dissolved in solution is applied to the microspheres by coating or impregnating the microspheres with the solution, separating the microspheres from the solution and drying the microspheres to deposit the catalyst on the inner and outer wall surfaces of the microspheres and on the particles forming the interconnecting voids in the walls of the microspheres.

35. The method of claim 33 wherein a catalyst support is first applied to the microspheres to deposit catalyst support on the inner and outer wall surfaces of the microspheres and on the particles forming the interconnecting voids in the walls of the microspheres and then applying a catalyst dissolved in solution to the microspheres containing the catalyst support, separating the microspheres from the solution and drying the microspheres to deposit the catalyst on the catalyst support.

36. The method of claim 33 wherein the microspheres contain substantially uniform size macro pores.

37. The method of claim 33 wherein the microspheres contain macro pores and the catalyst is applied through the macro pores into the single central cavity in the interior of the microspheres in the form of a melt, a sol dispersion or a slurry.

38. The method of claim 33 wherein the microspheres contain macro pores and a catalyst support is applied through the macro pores into the single central cavity in the interior of the microsphere in the form of a melt, a sol dispersion or a slurry, and a catalyst is then applied to the catalyst support.

39. The method of claim 38 wherein the catalyst is applied to the catalyst support in the form of a catalyst in solution.

40. The method of claim 38 wherein the catalyst is applied to the catalyst support in the form of a melt, a sol dispersion or a slurry.

41. The method of claim 37 wherein the microspheres are placed on a porous bed, the catalyst in the form of a melt, a sol dispersion or a slurry is applied to the microspheres, a suction is applied to the opposite side of the porous bed and the catalyst flows through the macro pores into the single central cavity of the microspheres.

42. The method of claim 38 wherein the microspheres are placed on a porous bed, the catalyst support in the form of a melt, a sol dispersion or a slurry is applied to the microspheres, a suction is applied to the opposite side of the porous bed and the catalyst support flows through the macro pores into the single central cavity of the microspheres and a catalyst is then applied to the catalyst support.

43. An auto emission control catalyst comprising hollow porous microspheres of substantially uniform diameter of 500 to 6000 microns and of substantially uniform wall thickness of 5.0 to 400 microns and macro pores 5.0 to 400 microns in size which extend through the walls, the walls of said microspheres comprise sintered together alumina particles which define interconnecting voids within the walls and a single central cavity in the interior of the microspheres and inner and outer microsphere wall surfaces, said interconnecting voids are continuous and extend from the outer wall surfaces to the inner wall surfaces, said walls have substantially uniform void content and said interconnecting voids are substantially uniformly distributed in the walls of the hollow microspheres, said microspheres have a catalyst selected from the group consisting of platinum, palladium and rhodium and mixtures thereof coated or impregnated on the inner and outer wall surfaces of the microspheres and on the particles forming the interconnecting voids in the wall of the microspheres, and the walls of said microspheres are free of latent solid or liquid blowing gas materials and are substantially free of relatively thinned wall portions or sections and bubbles.

44. The auto emission control microsphere catalysts of claim 43 wherein the microspheres are of substantially uniform diameter of about 1500 to 2000 microns, are of substantially uniform wall thickness of about 40–80 microns and the microspheres are substantially spherical in shape and contain a multiplicity of substantially uniform size macro pores about one hundred microns in diameter and the coated or impregnated catalyst comprises a mixture of platinum and palladium.

45. A hydrodinitrification and hydrodesulfurization catalyst comprising hollow porous microspheres of substantially uniform diameter of 500 to 6000 microns and of substantially uniform wall thickness of 5.0 to 400 microns, the walls of said microspheres comprise sintered together alumina particles which define interconnecting voids within the walls and a single central cavity in the interior of the microspheres and inner and outer microsphere wall surfaces, said interconnecting voids are continuous and extend from the outer wall surface to the inner wall surface, said walls have substantially uniform void content and said interconnecting voids are substantially uniformly distributed in the walls of the hollow microspheres, said microspheres have contained within the single central cavity and have within the interconnecting voids a catalyst selected from the group consisting of cobalt-molybdenum, nickel-molybdenum and nickel-tungsten and the oxides and sulfides thereof and mixtures thereof, and the walls of said microspheres are free of latent solid or liquid blowing gas materials and are substantially free of relatively thinned wall portions or sections and bubbles.

46. The hydrodinitrification and hydrodesulfurization microsphere catalyst of claim 45 wherein said microspheres have contained within the single central cavity and within the interconnecting voids a catalyst support and the catalyst support has coated or impregnated thereon the catalyst.

47. The hydrodinitrification and hydrodesulfurization microsphere catalyst of claim 45 wherein the microspheres are of substantially uniform diameter of 2000 to 4000 microns and are of substantially uniform wall thickness of 40 to 80 microns and the microspheres are substantially spherical in shape.

48. The hydrodinitrification microsphere catalyst of claim 45 wherein the catalyst is a member of the group consisting of nickel-molybdenum and nickel tungsten and the oxides and sulfides thereof and mixtures thereof.

49. The hydrodesulfurization microsphere catalyst of claim 45 wherein the catalyst is a member of the group consisting of cobalt-molybdenum and the oxides and sulfides thereof and mixtures thereof.

50. A hydrocracking catalyst comprising hollow porous microspheres of substantially uniform diameter of 500 to 6000 microns and of substantially uniform wall thickness of 5.0 to 400 micron wall thickness, the walls of said microspheres comprise sintered together alumina particles which define interconnecting voids within the walls and a single central cavity in the interior of the microspheres and inner and outer microsphere wall surfaces, said interconnecting voids are continuous and extend from the outer wall surfaces to the inner wall surfaces, said walls have substantially uniform void content and said interconnecting voids are substantially uniformly distributed in the walls of the hollow microspheres, said microspheres have contained within the single central cavity a nickel catalyst and the walls of said microspheres are free of latent solid or liquid blowing gas materials and are substantially free of relatively thinned wall portions or sections and bubbles.

51. The hydrocracking catalysts of claim 50 wherein said microspheres have contained within the single central cavity and within the interconnecting voids a catalyst support and the catalyst support hs coated or impregnated thereon the catalyst.

52. The hydrocracking catalysts of claim 50 wherein the microspheres are of substantially uniform diameter of 2000 to 4000 microns and are of substantially uniform wall thickness of 40 to 80 microns and the microspheres are substantially spherical in shape.

53. The hydrocracking catalysts of claim 50 wherein the microspheres contain within the single central cavity a nickel-alumina catalyst deposited on a catalyst support and have within the interconnecting voids a nickel-alumina catalyst deposited on a catalyst support.

54. The hydrocracking catalysts of claim 50 wherein the catalyst contained within the single central cavity is in the form of loose agglomerates of a lattice work of a nickel-alumina catalyst deposited on a silica catalyst support and the catalyst in the interconnecting voids is in the form of a latticework of nickel-alumina catalyst on a silica catalyst support.

* * * * *